(12) United States Patent
Urch et al.

(10) Patent No.: US 6,391,883 B1
(45) Date of Patent: May 21, 2002

(54) BICYCLIC AMINES

(75) Inventors: Christopher John Urch; Roger Salmon; Terence Lewis; Christopher Richard Ayles Godfrey, all of Bracknell; Martin Stephen Clough, Twyford, all of (GB)

(73) Assignee: Syngenta Limited (GB)

(*) Notice: Subject to any disclaimer, the term of this patent is extended or adjusted under 35 U.S.C. 154(b) by 0 days.

(21) Appl. No.: 09/602,711

(22) Filed: Jun. 26, 2000

Related U.S. Application Data

(62) Division of application No. 09/207,195, filed on Dec. 8, 1998, which is a division of application No. 08/651,182, filed on May 24, 1996, now Pat. No. 5,922,732.

(30) Foreign Application Priority Data

May 24, 1995 (GB) .............................. 9510459

(51) Int. Cl.[7] ..................... A61K 31/497; C07D 239/24
(52) U.S. Cl. ..................... 514/255; 514/256; 514/247; 544/238; 544/333; 544/405
(58) Field of Search .................. 544/238, 333, 544/336, 405; 514/255, 256, 247

(56) References Cited

U.S. PATENT DOCUMENTS

| | | | |
|---|---|---|---|
| 3,120,537 A | 2/1964 | Archer et al. | 260/291 |
| 3,133,073 A | 5/1964 | Archer | 260/292 |
| 3,308,131 A | 3/1967 | McKusick | 260/294 |
| 3,501,461 A | 3/1970 | Newallis et al. | 260/239 |
| 3,546,232 A | 12/1970 | Kaiser et al. | 260/292 |
| 3,556,943 A | 1/1971 | Fonken et al. | 195/51 |
| 3,657,257 A | 4/1972 | Helsley et al. | 260/292 |
| 4,180,669 A | 12/1979 | Winn | 546/240 |
| 4,393,069 A | 7/1983 | Langbein et al. | 424/265 |
| 4,590,270 A | 5/1986 | Kompis et al. | 544/320 |
| 4,774,249 A | 9/1988 | Kompis et al. | 514/272 |
| 5,491,148 A | 2/1996 | Berger et al. | 514/305 |
| 5,859,024 A * | 1/1999 | Hotson et al. | 546/124 |

FOREIGN PATENT DOCUMENTS

| | | |
|---|---|---|
| DE | 27 49 584 | 5/1978 |
| EP | 31219 | 7/1981 |
| EP | 0 216 625 | 4/1987 |
| EP | 0 307 142 | 3/1989 |
| EP | 0 315 390 | 5/1989 |
| EP | 0 398 578 | 11/1990 |
| EP | 0 498 331 | 8/1992 |
| EP | 0 518 805 | 12/1992 |
| FR | 2 548 666 | 1/1985 |
| GB | 1 061 472 | 3/1967 |
| GB | 1304649 | 1/1973 |
| WO | 91/17156 | 11/1991 |
| WO | 92/01688 | 2/1992 |
| WO | 93/00313 | 1/1993 |
| WO | 93/14636 | 8/1993 |
| WO | 93/25527 | 12/1993 |
| WO | 95/03306 | 2/1995 |
| WO | 96/08968 | 3/1996 |
| WO | 96/36637 | 11/1996 |
| WO | 96/37494 | 11/1996 |
| WO | 97/13770 | 4/1997 |
| WO | 97/43286 | 11/1997 |

OTHER PUBLICATIONS

CA 129:67708, Urch et al. 1998.*

Archer, S., et al., J. Am. Chem. Soc., "The Action of Nucleophilic Agents on 3 α–Chlorotropane," vol. 80, 1958, pp. 4677–4681.

(List continued on next page.)

*Primary Examiner*—Jane Fan
(74) *Attorney, Agent, or Firm*—Hale & Dorr LLP

(57) ABSTRACT

A compound of formula (I):

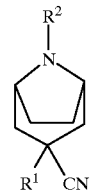

(I)

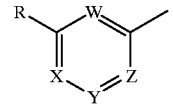

(A)

wherein $R^1$ represents a group of formula (A) where each of W, X, Y and Z and Z represents either a group CR or the nitrogen atom, provided that not more than two of W, X, Y and Z represent the nitrogen atom and where each R present is independently selected from hydrogen and halogen atoms and cyano, amino, hydrazino, acylamino, hydroxy, alkyl, hydroxyalkyl, alkoxy, haloalkyl, haloalkoxy, alkenyl, alkenyloxy, alkoxyalkenyl, alkynyl, carboxylic acyl, alkoxycarbonyl, aryl and heterocyclyl groups, said groups comprising up to 6 carbon atoms, and wherein $R^2$ represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; and acid addition salts and quaternary ammonium salts and N-oxide derived therefrom. The compounds are useful as insecticides.

23 Claims, No Drawings

OTHER PUBLICATIONS

Bell, M.R., et al., J. Am. Chem. Soc., "Ethyl 3 α–Phenyltropane–3β–carboxylate and Related Compounds," vol. 82, No. 7–9, 1960, pp. 4638–4641.

Gutkowska, B., et al., Acta Polon. Pharm., "Syntezy Niektorych Pochodnych 8–Alkilo–8–Aza–Bicyklo[3.2.1] Oktan–3–Onu," vol. 38, No. 4, 1981, pp. 411–415.

Lowe, J. A., et al., J. Med. Chem., "Aza–Tricyclic Substance P Antagonists," vol. 37, No. 18, 1994, p. 2831.

Maag, H., et al., Helvetica Chimica Acta, "94.5–(N–Arylnortropan–3–yl)– and 5–(N–Arylpiperidin–4–yl)–2,4–diaminopyrimidines. Novel Inhibitors of Dihydrofolate Reductase," vol. 69, No. 4, 1986, pp. 887–897.

Repke, D. B., et al., J. Org. Chem., "Abbreviated Ibogaine Congeners. Synthesis and Reactions of Tropan–3–yl–2– and –3–indoles. Investigation of an Unusual Isomerization of 2–Substituted Indoles Using Computational and Spectroscopic Techniques," vol. 59, No. 8, 1994, pp. 2164–2171.

Zirkle, C. L., et al., J. Org. Chem., "The Isomeric 3–Oxa– and 3–Thiagranatanin–7–ols and Their Derivatives; Reduction of Bicyclic Amino Ketones Related to Tropinone," vol. 26, 1961, pp. 395–407.

Daum et al., J. Med. Chem 18, 496 (1975).

Cignarella et al., JACS 83, 4999 (1961).

Chem. Abstr. 56, 14231g (1961).

* cited by examiner

BICYCLIC AMINES

This is a division of application Ser. No. 09/207,195 filed on Dec. 8, 1998 which in turn is a division of Ser. No. 08/651,182 filed May 24, 1976 U.S. Pat. No. 5,922,732 which issued Jul. 13, 1999.

This invention relates to novel bicyclic amines, to processes for preparing them, to insecticidal compositions comprising and to methods of combatting and controlling insect pests therewith.

The invention provides compounds of formula (I) wherein $R^1$ represents a group of formula (A) where each of W, X, Y and Z and Z represents either a group CR or the nitrogen atom, provided that not more than two W, X, Y and Z represent the nitrogen atom and where each R present is independently selected from hydrogen and halogen atoms and cyano, amino, hydrazino, acylamino, hydroxy, alkyl, hydroxyalkyl, alkoxy, haloalkyl, haloalkoxy, alkenyl, alkenyloxy, alkoxyalkenyl, alkynyl, carboxylic acyl, alkoxycarbonyl, aryl and heterocyclyl groups, said groups comprising up to 6 carbon atoms, and wherein $R^2$ represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl groups, said groups comprising from 1 to 15 carbon atoms, said groups being optionally substituted with one or more substituents selected from halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; and acid addition salts and quaternary ammonium salts and N-oxides derived therefrom. $R^1$ is preferably a halo-substituted phenyl, pyridyl or diazinyl group.

In a preferred aspect invention provides compounds of formula (I) were $R^1$ represents an optionally halogen substituted phenyl group or an optionally halogen substituted pyridyl, pyridazinyl or pyrazinyl group and $R^2$ represents hydrogen or a $C_{1-6}$ alkyl, alkenyl, alkynyl, phenyl, benzyl, pyridylmethyl, thienylmethyl, thiazolylmethyl group which may be optionally substituted with one or more alkyl, alkoxy, alkoxycarbonyl, cyano, optionally substituted alkane sulphonyl groups or halogen atoms; and acid addition salts thereof.

One particularly preferred group of compounds are those wherein $R^1$ represents an optionally halogen substituted phenyl or pyridyl group and $R^2$ represents a alkyl group containing up to 4 carbon atoms which may optionally be substituted with one or more halogen atoms.

An especially preferred group of compounds are those wherein $R^1$ represents a 5-halopyrid-3-yl group and $R^2$ represents hydrogen or a haloalkyl, haloalkenyl or halobenzyl group.

Specific compounds of formula I according to the invention include those set out in Table I below in which the groups represented by $R^1$ and $R^2$ are given for each compound, together with the melting point (° C.) or an indication of the physical state of the compound.

TABLE I

| Compound No | $R^1$ | $R^2$ | Melting Point |
|---|---|---|---|
| 1 | 3,5-dichlorophenyl | methyl | 145–146° C. |
| 2 | 3,5-difluorophenyl | methyl | 93–94° C. |
| 3 | 2,3-difluorophenyl | methyl | oil |
| 4 | pentafluorophenyl | methyl | oil |
| 5 | 2,3-dichlorophenyl | methyl | solid |
| 6 | 4-methoxyphenyl | benzyl (Isomer A) | 178.4° C. |
| 7 | 4-methoxyphenyl | benzyl (Isomer B) | 95–100° C. |
| 8 | phenyl | benzyl | 90–90.5° C. |
| 9 | 3,5-difluorophenyl | H | 112.1° C. |
| 10 | 3,5 difluorophenyl | benzyl | 85.2° C. |
| 11 | 3,5-difluorophenyl | 5,6-dichloropyrid-3-ylmethyl | 143.2–144.2° C. |
| 12 | 3,5-difluorophenyl | pyrid-2-ylmethyl | 127.9–128.5° C. |
| 13 | 3,5-difluorophenyl | 3-methylbenzyl | 95.9–96.1° C. |
| 14 | 3,5-difluorophenyl | 4-chlorobenzyl | 95.5–96.7° C. |
| 15 | 3,5-difluorophenyl | pyrid-3-ylmethyl | 78.2° C. |
| 16 | 3,5-difluorophenyl | 3,4-methylenedioxybenzyl | oil |
| 17 | 3,5-difluorophenyl | 3,5-dichlorobenzyl | 154.1° C. |
| 18 | 3,5-difluorophenyl | 3,3-difluoroprop-2-en-1-yl | 94.6° C. |
| 19 | 3,5-difluorophenyl | 2-hydroxy-2-phenylethyl | 120.8° C. |
| 20 | 3,5-difluorophenyl | 1-phenyl-2-hydroxyethyl | 168.8° C. |
| 21 | 3,5-difluorophenyl | allyl | 70.5° C. |
| 22 | 3,5-difluorophenyl | propargyl | 108.4° C. |
| 23 | 3,5-difluorophenyl | 2-fluoroethyl | oil |
| 24 | 3,5-difluorophenyl | 2-hydroxyethyl | 100.4° C. |
| 25 | 3,5-difluorophenyl | 2-methoxyethyl | 54.8° C. |
| 26 | 3,5-difluorophenyl | 2-cyanoethyl | 115° C. |
| 27 | 3,5-difluorophenyl | 5-chlorothien-2-ylmethyl | 114° C. |
| 28 | 3,5-difluorophenyl | 6-chloropyrid-2-yl | gum |
| 29 | 3,5-difluorophenyl | 2-methylthiazol-5-ylmethyl | 140° C. |
| 30 | 3,5-difluorophenyl | 2-iminyl-2-methoxyethyl | 109° C. |
| 31 | phenyl | benzyl (exo-isomer) | 115–116° C. |
| 32 | phenyl | benzyl (endo-isomer) | 97° C. |
| 33 | pyrid-3-yl | methyl | 87° C. |
| 34 | pyrid-3-yl | 2-fluoroethyl | 86–88° C. |
| 35 | pyrid-3-yl | allyl | 90–92° C. |
| 36 | pyrid-3-yl | H | 80–81° C. |
| 37 | pyrid-3-yl | benzyl | 119–120° C. |
| 38 | pyrid-3-yl | ethyl | oil |
| 34 | pyrid-3-yl | 2-fluoroethyl | 86–88° C. |
| 35 | pyrid-3-yl | allyl | 90–92° C. |
| 36 | pyrid-3-yl | H | 80–81° C. |
| 37 | pyrid-3-yl | benzyl | 119–120° C. |
| 38 | pyrid-3-yl | ethyl | oil |
| 39 | pyrid-3-yl | t-butoxycarbonylmethyl | gum |
| 40 | N-methylpyridinium-3-yl | t-butoxycarbonyl (iodide) | 185–187° C. |
| 41 | 6-chloropyridazin-3-yl | methyl | 119–120° C. |
| 42 | pyrid-3-yl | propyl | oil |
| 43 | 6-chloropyrazin-2-yl | methyl | 80° C. |
| 44 | pyrid-3-yl | methane-sulphonylmethylsulphonyl | 163–164° C. |
| 45 | pyrid-3-yl | methane-sulphonyl | 135° C. |
| 46 | 6-chloropyrid-3-yl | methyl | gum |
| 47 | pyrid-3-yl | methoxymethyl | oil |
| 48 | pyrid-3-yl | ethoxymethyl | oil |
| 49 | pyrid-3-yl | cyanomethyl | 90–91° C. |
| 50 | pyrid-3-yl | ethoxycarbonylmethyl | gum |
| 51 | pyrid-3-yl | methoxycarbonylmethyl | gum |
| 52 | 2-fluoro-4-nitrophenyl | methyl | 100–102° C. |
| 53 | 3-fluorophenyl | methyl | oil |
| 54 | pyrid-3-yl | 2-hydroxyethyl | 155.2–156.8° C. |
| 55 | 5,6-dichloropyrid-3-yl | methyl | 110.1–111.4° C. |

TABLE I-continued

| Compound No | R$^1$ | R$^2$ | Melting Point |
|---|---|---|---|
| 56 | pyrid-3-yl | propargyl | 119-8–121.1° C. |
| 57 | pyrid-3-yl | methyl | gum |
| 58 | pyrid-3-yl | but-2-en-1-yl | 193–194° C. |
| 59 | 3,5-difluorophenyl | 4-nitrophenyl | 96.9–97.9° C. |
| 60 | 5-chloropyrid-3-yl | methyl | 152.8–154.5° C. |
| 61 | pyrid-3-yl | phenyl | 136–137° C. |
| 62 | pyrazin-2-yl | methyl | 76–76.9° C. |
| 63 | 2,6-dichloropyrimid-4-yl | methyl | 95.3–96.8° C. |
| 64 | 5-chloropyrid-3-yl | 2-fluoroethyl | 125.9–126.9° C. |
| 65 | 2,6-dichloropyrid-4-yl | methyl | 165–165.8° C. |
| 66 | 2-chloro-6-hydrazinopyrid-4-yl | methyl | 72–73° C. |
| 67 | pyrid-4-yl | methyl | 74.5–76.1° C. |
| 68 | 5-bromopyrid-3-yl | methyl | 144.1–145.2° C. |
| 69 | 5-chloropyrid-3-yl | vinyloxycarbonyl | gum |
| 70 | 5-chloropyrid-3-yl | H | 85–87° C. |
| 71 | 6-chloropyrid-2-yl | methyl | 103.9–104.8° C. |
| 72 | 5-chloropyrid-3-yl | 2,2,2-trifluoroethyl | 109.5–111.5° C. |
| 73 | 3,5-difluorophenyl | pyrid-2-yl | oil |
| 74 | 5-chloropyrid-3-yl | phenyl | 122–123° C. |
| 75 | 5-chloropyrid-3-yl | propargyl | 110–112° C. |
| 76 | 5-chloropyrid-3-yl | allyl | 78–80° C. |
| 77 | 5-methoxypyrid-3-yl | methyl | 112.2–113.1° C. |
| 78 | 5-chloropyrid-3-yl | ethyl | 116–118° C. |
| 79 | 5-chloropyrid-3-yl | butyl | 48–50° C. |
| 80 | 5-ethoxypyrid-3-yl | methyl | 567.2–57° C. |
| 81 | 5-chloropyrid-3-yl | hexyl | resin |
| 82 | 5-chloropyrid-3-yl | phenoxycarbonyl | 117–123° C. |
| 83 | 5-chloropyrid-3-yl | 2,2,2-trichloroethoxycarbonyl | oil |
| 84 | 5-chloropyrid-3-yl | ethoxycarbonyl | oil |
| 85 | 5-chloropyrid-3-yl | fluoren-9-ylmethyloxycarbonyl | 68–70° C. |
| 86 | 5-chloropyrid-3-yl | ethoxycarbonylmethyl | gum |
| 87 | 5-chloropyrid-3-yl | isopropyl | oil |
| 88 | 5-chloropyrid-3-yl | 4,4,4-trifluorobut-3-on-1-en-1-yl | 143.9–145.1° C. |
| 89 | 5-chloropyrid-3-yl | 1-methyl-2,2,2-trichloroethoxycarbonyl | 152–155° C. |
| 90 | 5-chloropyrid-3-yl | allyloxycarbonyl | oil |
| 91 | 5-chloropyrid-3-yl | benzyloxycarbonyl | oil |
| 92 | 5-chloropyrid-3-yl | 2-chloroethoxycarbonyl | gum |
| 93 | 5-chloropyrid-3-yl | pentafluorobenzyl | 143–144° C. |
| 94 | 5-chloropyrid-3-yl | nitrophenyl | 213–214.5° C. |
| 95 | 5-chloropyrid-3-yl | acetyl | 162–165° C. |
| 96 | 5-chloropyrid-3-yl | trifluoroacetyl | 121–124° C. |
| 97 | 5-chloropyrid-3-yl | 4-chlorobenzoyl | 175–177° C. |
| 98 | 5-chloropyrid-3-yl | 4-fluorobenzoyl | 200–204° C. |
| 99 | 5-chloropyrid-3-yl | 3-fluoropropyl | oil |
| 100 | 5-chloropyrid-3-yl | 2,4-bis(trifluoromethyl)benzyl | 112–114° C. |
| 101 | 5-chloropyrid-3-yl | 4-carboxybenzyl | gum |
| 102 | 5-(prop-1-enyloxy)-pyrid-3-yl | methyl | gum |
| 103 | 5-chloropyrid-3-yl | 2,3-difluorobenzyl | 102–103° C. |
| 104 | 5-chloropyrid-3-yl | 2-phenylethyl | oil |
| 105 | 5-chloropyrid-3-yl | 4-cyanophenyl | 201–204° C. |
| 106 | 5-chloropyrid-3-yl | 3,3-difluoroprop-2-en-1-yl | oil |
| 107 | 5-chloropyrid-3-yl | carboxymethyl | 165–167° C. |
| 108 | 5-chloropyrid-3-yl | 3,5-dibromobenzyl | 194–196° C. |
| 109 | 5-chloropyrid-3-yl | 3-chloro-4-fluorobenzyl | 95–97° C. |
| 110 | 5-chloropyrid-3-yl | formyl | 141–142° C. |
| 111 | 5-chloropyrid-3-yl | isopropoxycarbonyl | gum |
| 112 | 5-chloropyrid-3-yl | benzenesulfonyl | 210–211° C. |
| 113 | 5-chloropyrid-3-yl | 2,4,6-trifluorobenzyl | 106–107° C. |
| 114 | 5-chloropyrid-3-yl | 2,3,6-trifluorobenzyl | 125–127° C. |
| 115 | 5-chloropyrid-3-yl | 1-cyano-1-phenylmethyl | 141–142° C. |
| 116 | 5-chloropyrid-3-yl | methoxycarbonyl | oil |
| 117 | 5-chloropyrid-3-yl | pyrid-2-ylmethyl | 123–125° C. |
| 118 | 5-chloropyrid-3-yl | pyrid-3-ylmethyl | 105–107° C. |
| 119 | 5-chloropyrid-3-yl | pyrid-4-ylmethyl | 111–114° C. |
| 120 | pyrid-2-yl | 2-fluoroethyl | 82–84° C. |
| 121 | 5-chloropyrid-3-yl | (R)-1-phenylethyl | 115.6–116.7° C. |
| 122 | 5-chloropyrid-3-yl | (S)-1-phenylethyl | 113.4–115° C. |
| 123 | 5-chloropyrid-3-yl | 2-methylthiazol-4-ylmethyl | 81–83° C. |
| 124 | 5-chloropyrid-3-yl | 3,5-dimethylisoxazol-4-ylmethyl | 95–99° C. |
| 125 | 5-chloropyrid-3-yl | 5-chlorothien-2-ylmethyl | 119–121° C. |
| 126 | 5-chloropyrid-3-yl | 5-trifluoromethyl-pyrid-2-yl | 124.5–125.5° C. |
| 127 | pyrid-3-yl | 2-methoxyethyl | 251–253° C. |
| 128 | 5-chloropyrid-3-yl | 6-fluoropyrid-2-yl | 131.5–132.5° C. |
| 129 | 5-chloropyrid-3-yl | 4-fluorophenyl | solid |
| 130 | 5-chloropyrid-3-yl | 2,2,3,3,3-pentafluoropropyl | oil |
| 131 | 5-chloropyrid-3-yl | 2,2,3,3-tetrafluoropropyl | 110–113° C. |
| 132 | 5-chloropyrid-3-yl | 2,2,3,3,4,4,4-heptafluoropropyl | oil |
| 133 | 5-chloropyrid-3-yl | 2,2,3,3,4,4,5,5-octafluoropropyl | oil |
| 134 | 5-aminopyrid-3-yl | methyl | 188–190° C. |
| 135 | 5-chloropyrid-3-yl | 1-phenyl-1-carboxamidomethyl | 193–195° C. |
| 136 | 5-chloropyrid-3-yl | 6-trifluoromethyl-pyrid-2-yl | 117.5–118.5° C. |
| 137 | 5-chloropyrid-3-yl | 6-chloropyrid-2-yl | 176–177° C. |
| 138 | 5-chloropyrid-3-yl | mercaptothiocarbonyl | 224° C. |
| 139 | 5-chloropyrid-3-yl | t-butyl | 127–129° C. |
| 140 | 5-chloropyrid-3-yl | 2-(ethoxycarbonyl)ethyl | gum |
| 141 | 5-chloropyrid-3-yl | 2-carboxyethyl | 180–181° C. |
| 142 | 5-chloropyrid-3-yl | 2,2-difluoroethyl | 101–104° C. |
| 143 | 5-bromopyrid-3-yl | 2,2,2-trifluoroethyl | 105–110° C. |
| 144 | 5-chloropyrid-3-yl | fluorocarbonyl | 165–167° C. |
| 145 | 5-chloropyrid-3-yl | N-methyl-N-phenyl carbamyl | 108–110° C. |
| 146 | 5-chloropyrid-3-yl | N-t-butylcarbamyl | 62–65° C. |
| 147 | 5-iodopyrid-3-yl | methyl | 144–145° C. |
| 148 | 5-hydroxypyrid-3-yl | methyl | 170.9–171.7° C. |
| 149 | 5-chloropyrid-3-yl | 4-morpholinocarbonyl | 143–145° C. |
| 150 | 5-cldoropyrid-3-yl | N,N-diisopropylcarbamyl | 118–121° C. |
| 151 | 5-chloropyrid-3-yl | pentafluorophenyl | gum |
| 152 | 5-chloropyrid-3-yl | 6-chloropyrimin-4-yl | 174–176° C. |
| 153 | 5-chloropyrid-3-yl | 2-acetamidothiazol-4-ylmethyl | solid |
| 154 | 5-chloropyrid-3-yl | N-(3-chloro-4-fluorophenyl) carbamyl | 216–218° C. |
| 155 | 5-chloropyrid-3-yl | 5-chloropyrid-3-yl | gum |
| 156 | 5-chloropyrid-3-yl | trifluoromethylpyrid-3-carboxamidomethyl | 149.3–150.4° C. |
| 157 | 5-chloropyrid-3-yl | 4-trifluoromethylpyrid-3-ylcarbonyl | 80.3–81.9° C. |
| 158 | 5-chloropyrid-3-yl | 5-chloro-1,2,3-triadiazol-4-ylmethyl | oil |
| 159 | 5-chloropyrid-3-yl | 1-formyl-1-phenylethyl | 124–126° C. |
| 160 | 5-chloropyrid-3-yl | 4,4,4-trifluorobutyl | oil |
| 161 | 5-methoxypyrid-3-yl | 2,2,2-trifluoroethyl | 88–90° C. |
| 162 | 5-chloropyrid-3-yl | 4-ethoxycarbonylphenyl | 131.5–132.5° C. |
| 163 | 5-chloro-6-fluoro pyrid-3-yl | 2,2,2-trifluoroethyl | 121–122° C. |
| 164 | 5-chloropyrid-3-yl | vinyloxycarbonyl | gum |
| 165 | 5-acetamidopyrid-3-yl | methyl | 195–197° C. |
| 166 | 5-methoxypyrid-3-yl | cyanomethyl | solid |

TABLE I-continued

| Compound No | R¹ | R² | Melting Point |
|---|---|---|---|
| 167 | 5-chloropyrid-3-yl | 3-chloromethyl-1,2,4-thiadiazol-5-yl | gum |
| 168 | 5-chloropyrid-3-yl | 5-chlorothiazol-2-yl | 111–112° C. |
| 169 | 5-chloropyrid-3-yl | cyano | 168–170° C. |
| 170 | 5-chloropyrid-3-yl | 4-carboxyphenyl | solid |
| 171 | 5-methoxypyrid-3-yl | vinyloxycarbonyl | gum |
| 172 | 5-methoxypyrid-3-yl | H | 112–114° C. |
| 173 | 5-chloropyrid-3-yl | 4-chlorophenyl | 137.5–138° C. |
| 174 | 5-trifluoromethyl-pyrid-3-yl | methyl | 118.2–118.5° C. |
| 175 | 5-chloropyrid-3-yl | 2-phenylbut-3-en-2-yl | gum |
| 176 | 5-chloropyrid-3-yl | 3-hydroxy-2-phenyl-prop-2-yl | 124–126° C. |
| 177 | 5-trifluoromethyl-pyrid-3-yl | formyl | 117–121° C. |
| 178 | 5-chloropyrid-3-yl | 3-acetoxy-2-phenyl-prop-2-yl | 130–131° C. |
| 179 | 5-chloropyrid-3-yl | 2-fluoro-2-phenyl-prop-1-yl | gum |
| 180 | 5-chloropyrid-3-yl | 3,3,5-trimethylhexyl | |
| 181 | 5-bromopyrid-3-yl | vinyloxycarbonyl | 63–66° C. |
| 182 | 5-chloropyrid-3-yl | pyrimid-2-yl; | 148.5–149.5° C. |
| 183 | 5-trifluoromethyl pyrid-3-yl | vinyloxycarbonyl | resin |
| 184 | 5-trifluoromethyl-pyrid-3-yl | H | resin |
| 185 | pyrid-3-yd | vinyloxycarbonyl | gum |
| 186 | 5-trifluoromethyl-pyrid-3-yl | 3-chlorobenzyl | oil |
| 187 | 5-chloropyrid-3-yl | 2-chloropyrimid-4-yl | 210–212° C. |
| 188 | 5-chloropyrid-3-yl | 4-trifluoromethyl-phenyl | 131–132° C. |
| 189 | 5-(pyrrol-1-yl)pyrid-3-yl | methyl | gum |
| 194 | pyrimid-4-yl | methyl | solid |
| 195 | 5-(1-ethoxyvinyl)-pyrid-3-yl | methyl | gum |
| 196 | pyrid-3-yl | 1,1-dimethylpropyl | gum |
| 197 | 5-chloropyrid-3-yl | 1-ethoxycarbonylethyl | gum |
| 198 | 5-bromopyrimid-4-yl | methyl | 141–145° C. |
| 199 | 5-trifluoromethyl-pyrid-3-yl | 2,2,2-trifluoroethyl | gum |
| 200 | 6-pyrimid-4-ylpyrimid-4-yl | methyl | 136–154° C. |
| 201 | 5-acetylpyrid-3-yl | methyl | gum |
| 202 | 5-fluoropyrid-3-yl | methyl | 135–137° C. |
| 203 | 5-bromopyrid-3-yl | H | 128–130° C. |
| 204 | 5-bromopyrid-3-yl | 2-chlorobenzyl | 109–111° C. |
| 205 | 5-chloropyrid-3-yl | 2-(3-chlorophenyl)-prop-2-yl | gum |
| 206 | 5-(2-hydroxyprop-2-yl)pyrid-3-yl | methyl | gum |
| 207 | 5-chloropyrid-3-yl | 2-methylbut-3-yn-2-yl | 107–110° C. |
| 208 | 5-bromopyrid-3-yl | ethoxycarbonyl | 92–94° C. |
| 209 | 5-chloropyrid-3-yl | 2-methyl-1,1,1-trifluoroprop-2-yl | 97–99° C. |
| 210 | 5-bromopyrid-3-yl | 2-methylpropyl | oil |
| 211 | 5-chloropyrid-3-yl | 1-methoxycarbonyl-ethyl (Isomer A) | gum |
| 212 | 5-chloropyrid-3-yl | 1-methoxycarbonyl-ethyl (racemate) | 105–106° C. |
| 213 | 5-chloropyrid-3-yl | 1-methoxycarbonyl-ethyl (Isomer B) | gum |
| 214 | 6-methoxypyrazin-2-yl | methyl | gum |
| 215 | 5-chloropyrid-3-yl | 1-cyano-1-(3-chlorophenyl)methyl | foam |
| 216 | 5-chloropyrid-3-yl | 1-cyanoethyl | gum |
| 217 | 5-phenylpyrid-3-yl | vinyloxycarbonyl | gum |
| 218 | 5-chloropyrid-3-yl | 4,4-difluorobut-3-en-1-yl | oil |
| 219 | 5-chloropyrid-3-yl | 1-cyano-2-methylprop-1-yl | gum |
| 220 | 5-phenylpyrid-3-yl | H | gum |
| 221 | 5-methylpyrid-3-yl | vinyloxycarbonyl | gum |
| 222 | 5-ethoxycarbonylpy-rid-3-yl | vinyloxycarbonyl | solid |
| 223 | 5-chloropyrid-3-yl | 2-cyanoprop-2-yl | solid |
| 224 | 6-ethynylpyrazin-2-yl | methyl | solid |
| 225 | 5-ethoxycarbonylpy-rid-3-yl | H | gum |
| 226 | 5-(2,2,2-trifluoroethoxy)-pyrid-3-yl | trifluoroethyl | oil |
| 227 | 5-chloropyrid-3-yl | 3-5-bis(trifluoromethyl)-benzyl | |
| 228 | 5-chloropyrid-3-yl | 2,6-difluorobenzyl | |
| 229 | 5-chloropyrid-3-yl | 3-phenoxybenzyl | |
| 230 | 5-chloropyrid-3-yl | 3-bromo-4-fluorobenzyl | |
| 231 | 5-chloropyrid-3-yl | 3-benzoylbenzyl | |
| 232 | 5-chloropyrid-3-yl | 3-(2,6-dichloro-benzoyl)benzyl | |
| 233 | 5-chloropyrid-3-yl | 3-(2,6-difluoro-benzoyl)benzyl | |
| 234 | 5-chloropyrid-3-yl | 4-allyl-2,3,5,6-tetrafluorobenzyl | |
| 235 | 5-chloropyrid-3-yl | 3-trifluoromethoxy-benzyl | |
| 236 | 5-chloropyrid-3-yl | naphth-1-ylmethyl | |
| 237 | 5-chloropyrid-3-yl | benzyl | |
| 238 | 5-chloropyrid-3-yl | 2-bromobenzyl | |
| 239 | 5-chloropyrid-3-yl | 2-methylbenzyl | |
| 240 | 5-chloropyrid-3-yl | 3-bromobenzyl | |
| 241 | 5-chloropyrid-3-yl | 3-methoxycarbonyl-benzyl | |
| 242 | 5-chloropyrid-3-yl | 3-methylbenzyl | |
| 243 | 5-chloropyrid-3-yl | 4-bromobenzyl | |
| 244 | 5-chloropyrid-3-yl | 4-methoxycarbonyl-benzyl | |
| 245 | 5-chloropyrid-3-yl | 4-t-butylcarbonyl-benzyl | |
| 246 | 5-chloropyrid-3-yl | 4-t-butylbenzyl | |
| 247 | 5-chloropyrid-3-yl | 4-isopropylbenzyl | |
| 248 | 5-chloropyrid-3-yl | 4-methylbenzyl | |
| 249 | 5-chloropyrid-3-yl | 3,4-difluorobenzyl | |
| 250 | 5-chloropyrid-3-yl | 2-fluorobenzyl | |
| 251 | 5-chloropyrid-3-yl | 3-bromo-5-fluoro-benzyl | |
| 252 | 5-chloropyrid-3-yl | 2,4-difluorobenzyl | |
| 253 | 5-chloropyrid-3-yl | 3-fluorobenzyl | |
| 254 | 5-chloropyrid-3-yl | 4-fluorobenzyl | |
| 255 | 5-chloropyrid-3-yl | 3-trifluoromethyl-benzyl | |
| 256 | 5-chloropyrid-3-yl | 4-trifluoromethyl-benzyl | |
| 257 | 5-chloropyrid-3-yl | 2-fluoro-3-chloro-benzyl | |
| 258 | 5-chloropyrid-3-yl | 2-chloro-3,6-difluorobenzyl | |
| 259 | 5-chloropyrid-3-yl | 2-chlorobenzyl | |
| 260 | 5-chloropyrid-3-yl | 2,6-dichlorobenzyl | |
| 261 | 5-chloropyrid-3-yl | 3-chlorobenzyl | |
| 262 | 5-chloropyrid-3-yl | 2-iodo-4-fluorobenzyl | 108–109° C. |
| 263 | 5-chloropyrid-3-yl | 2-fluoro-3-methyl-benzyl | |
| 264 | 5-chloropyrid-3-yl | 2-(N-succinimido)-benzyl | |
| 265 | 5-chloropyrid-3-yl | 2-fluoro-5-trifluoromethylbenzyl | |
| 266 | 5-chloropyrid-3-yl | biphenyl-2-ylmethyl | |
| 267 | 5-chloropyrid-3-yl | 2-cyanobenzyl | |
| 268 | 5-chloropyrid-3-yl | 4-(1,2,3-thiadiazol-4-yl)benzyl | |
| 269 | 5-chloropyrid-3-yl | 3-(4-fluorophenoxy)-benzyl | |
| 270 | 5-chloropyrid-3-yl | 4-cyanobenzyl | |

TABLE I-continued

| Compound No | R¹ | R² | Melting Point |
|---|---|---|---|
| 271 | 5-chloropyrid-3-yl | 2,3,4-trifluorobenzyl | |
| 272 | 5-chloropyrid-3-yl | 2-nitrobenzyl | |
| 273 | 5-chloropyrid-3-yl | 2-nitro-6-fluorobenzyl | |
| 274 | 5-chloropyrid-3-yl | 3-nitrobenzyl | |
| 275 | 5-chloropyrid-3-yl | 4-nitrobenzyl | |
| 276 | 5-chloropyrid-3-yl | 2-methylprop-1-yl | |
| 277 | 5-chloropyrid-3-yl | decyl | |
| 278 | 5-chloropyrid-3-yl | 2-phenoxyethyl | |
| 279 | 5-chloropyrid-3-yl | 2-ethoxyethyl | |
| 280 | 5-chloropyrid-3-yl | 3-methylbut-1-yl | |
| 281 | 5-chloropyrid-3-yl | 3-methoxycarbonyl-prop-1-yl | |
| 282 | 5-chloropyrid-3-yl | 3-phenylprop-1-yl | |
| 283 | 5-chloropyrid-3-yl | cyclohexylmethyl | |
| 284 | 5-chloropyrid-3-yl | 2-cyanoethyl | |
| 285 | 5-chloropyrid-3-yl | 3-cyanoprop-1-yl | |
| 286 | 5-chloropyrid-3-yl | 2-hydroxyprop-1-yl | |
| 287 | 5-chloropyrid-3-yl | 2-propenoyloxyethyl | |
| 288 | 5-chloropyrid-3-yl | 2-methoxyethyl | |
| 289 | 5-chloropyrid-3-yl | tetrahydropyran-2-yl-methyl | |
| 290 | 5-chloropyrid-3-yl | 2-hydroxymethyl-prop-1-yl | |
| 291 | 5-chloropyrid-3-yl | diethylphosphono-methyl | 69–70° C. |
| 292 | 5-chloropyrid-3-yl | phosphonomethyl | 242–245° C. |
| 293 | 5-chloropyrid-3-yl | methyl (N-oxide) | 153–155° C. |
| 294 | pyrid-3-yl | t-butoxycarbaryl | |
| 295 | 6-choloropyrid-3-yl | H | |
| 296 | 5-chloropyrid-3-yl | methoxy | |
| 297 | 2-chloropyrimid-4-yl | 2,2,2-trifluoroethyl | |
| 298 | 6-chloropyrazin-2-yl | vinyloxycarbonyl | |
| 299 | 6-chloropyrazin-2-yl | H | |
| 300 | 6-chloropyrazin-2-yl | 3-chlorobenzyl | |
| 301 | 6-chloropyrazin-2-yl | cyanomethyl | |
| 302 | 5-chloropyrid-3-yl | 1-(3-chlorophenyl)-ethyl | |
| 303 | 5-chloropyrid-3-yl | 4-methoxyphenyl | |
| 304 | 5-cyanopyrid-3-yl | methyl | |
| 305 | 2-chloropyrid-4-yl | methyl | |
| 306 | 5-chloropyrid-3-yl | 2-phenylprop-1-en-1-yl | |
| 307 | 5-chloropyrid-3-yl | methylmercaptothiocarbonyl | |
| 308 | 5-(2,2,2-trifluoroethoxy)pyrid-3-yl | methyl | |
| 309 | 5-iodopyrid-3-yl | vinyloxycarbonyl | |

It will be appreciated that the bicyclic amine compounds of formula I are capable of existing in more than one isomeric form since the groups R¹ and R² may be positioned in either an exo or endo relationship, and the present invention embraces within its scope both exo and endo forms and mixtures thereof and also any further isomeric variants arising from cis and trans substitution patterns or chiral centres present in either of R¹ or R². Suitable acid addition salts include those with an inorganic acid such as hydrochloric, hydrobromic, sulfuric, nitric and phosphoric acids, or an organic carboxylic acid such as oxalic, tartaric, latic, butyric, toluic, hexanoic and phthalic acids, or sulplhonic acids such as methane, benzene and toluene sulphonic acids. Examples of salts of compound 72 (Table I) with some less common acids are given in Table IA.

TABLE IA

| Compound No | Acid Component |
|---|---|
| 310 | 2-chlorobenzoic acid |
| 311 | 4-chlorophenoxyacetic acid |
| 312 | 2,4,6-trimethylbenzoic acid |
| 313 | 3-benzylbenzoic |
| 314 | 4-hydroxybenzoic acid |
| 315 | 1-phenylpropionic acid |
| 316 | 3-(4-hydroxyphenyl)propenoic acid |
| 317 | undecanoic acid |
| 318 | 4-(4-hydroxyphenyl)butyric acid |
| 319 | 2-hydroxy-5-nitrobenzoic acid |
| 320 | 2-nitro-5-N-methylformamidobenzoic acid |
| 321 | 2,2,3,3-tetramethylcyclopropanoic acid |

The preparation of the compounds of formula (I) may be accomplished by use of one or more of the following synthetic techniques described below and further illustrated in the Examples.

The compounds of general formula (I) can be prepared from compounds of general formula (II) by treating them with a suitable base, such as potassium carbonate, in the presence of compound of formula $R^2$ where L is a suitable leaving group such as a halide or triflate.

Alternatively, compounds of general formula (I) can be prepared from compounds of general formula (II) by reductive amination with an aldehyde ($R^3$CHO; where $R^3CH_2=R^2$) in the presence of a suitable reducing agent such as formic acid.

Compounds of general formula (II) can be prepared by demethylating compound of general formula (III) by, for instance, treating them first with a chloroformate ester (such as vinyl chloroformate) to produce a carbamate, followed by acid hydrolysis.

Compounds of general formula (III) can be prepared by treating 3-cyano-8-methyl-8-azabicyclo[3.2.1]octane (IV) first with a suitable base, such as lithium diisopropylamide (LDA), followed by reaction with an aryl or heteroaryl halide ($R^1$Hal).

3-Cyano-8-methyl-8-azabicyclo[3.2.1]octane (IV) can be prepared by treating tropinone (V) with tosylmethyl isocyanide in the presence of a suitable base, such as potassium ethoxide. As an alternative 3-cyano-8-methyl-8-azabicyclo[3.2.1]octane (IV) can be prepared from tropine (XII) by treatment with thionyl chloride to give alternative 3-chloro-8-methyl-8-azabicyclo[3.2.1]octane (XIII) followed by treatment with cyanide as described in J. Am. Chem. Soc., 1958 80, 4677.

As an alternative, compounds of general formula (I) can be prepared from compounds of general formula (VI) by treatment with a suitable base, such as lithium diisopropylamide (LDA), followed by reaction with an aryl or heteroaryl halide ($R^1$Hal).

Compounds of general formula (VI) can be prepared from 3cyano-8-azabicyclo[3.2.1]octane (VII) by treatment with a suitable base, such as potassium carbonate, in the presence of an alkyl halide ($R^2$Hal).

3Cyano-8-azabicyclo[3.2.1]octane (VII) can be prepared by demethylating 3-cyano-8-methyl-8-azabicyclo[3.2.1]octane (IV) by, for instance, treatment first with a chloroformate ester (such as vinyl chloroformate) to produce a carbamate, followed by acid hydrolysis.

As a further alternative, compounds of general formula (VI) can be prepared by treating compounds of general formula (VIII) with tosylmethyl isocyanide in the presence of a suitable base, such as potassium ethoxide.

Compounds of general formula (VIII) can be prepared by the Robinson tropinone synthesis, see, for instance, J. Chem. Soc., 1917, 111, 762. As an alternative compounds of general formula (VIII) can be prepared from cyclohepta-2, 6-dienone (XI) by reaction with an amine ($R^2NH_2$) as described in, for instance, Tetrahedron, 1973, 155, Bull, Chem, Chem, Soc, Jpn., 1971, 44, 1708 and J. Org. Chem., 1971, 36, 1718.

As yet a further alternative, compounds of general formula (I) can be prepared by treatment of a compound of general formula (IX) with an aryl- or heteroaryl-acetonitrile of general formula (X) in the presence of a suitable base, such as sodium hydride, as described in J. Med. Chem., 1975, 18, 496.

The compounds of general formula (VI) (except those where $R^2$ represents methyl, benzyl or trichloroethyl are believed not to have been previously described. Accordingly in a further aspect the invention provides compounds of formula (VI) wherein $R^2$ has any of the meanings given hereinabove except that $R^2$ cannot be methyl, benzyl or trichloroethyl.

In a further aspect the invention provides a method of combating insect and like pests at a locus by applying to the locus or the pests an insecticidally-effective amount of an insecticidal composition comprising the compounds of Formula I or an acid addition salt thereof.

The compounds of Formula I and acid addition salts thereof may be used to combat and control infestations of insect pests such as Lepidoptera, Diptera, Homoptera and Coleoptera (including Diabroctica i.e. corn rootworms) and also other invertebrate pests, for example, acarine pests. The insect and acarine pests which may be combated and controlled by the use of the invention compounds include these pests associated with agriculture (which term includes the growing of crops for food and fibre products), horticulture and animal husbandry, foresty, the storage of products of vegetable origin, such as fruit, grain and timber, and also those pests associated with the transmission of diseases of man and animals. Examples of insect and acarine pest species which may be controlled by the compounds of Formula I include:
*Myzus persicae* (aphid), *Aphis gossypii* (aphid), *Aphis fabae* (aphid), *Aedes aegypti* (mosquito), Anopheles spp. (mosquitos), Culex spp. (mosquitos), *Dysdercus fasciatus* (capsid), *Musca domestica* (housefly), *Pieris brassicae* (white butterfly), *Plutella xylostella* (diamond back moth), *Phaedon cochleariae* (mustard beetle), Aonidiella spp. (scale insects), Trialeurodes spp. (white flies), *Bemisia tabaci* (white fly), *Blatella germanica* (cockroach), *Periplaneta americana* (cockroach), *Blatta orientalis* (cockroach) *Spodoptera littoralis* (cotton leafworm), *Heliothis virescens* (tobacco budworm) *Chortiocetes terminifera* (locust), Diabrotica spp. (rootworms), Argotis spp. (cutworms), *Chilo partellus* (maize stem borer), *Nilaparvata lugens* (panthopper), *Nephotettix cincticeps* (leafhopper), *Panonychus ulmi* (European red mite), *Panonychus citri* (citrus red mite), *Tetranychus urticae* (two-spotted spider mite), *Tetranychus cinnabarinus* (carmine spider mite), *Phyllcoptruta oleivora* (citrus rust mite), *Polyphagotarsonemus latus* (broad mite) and Brevipalpus spp. (mites).

In order to apply the compounds of Formula I to the locus of the nematode, insect or acarid pest, or to a plant susceptible to attack by the nematode, insect or acardi pest, the compound is usually formulated into a composition which includes in addition to the the compounds of Formula I suitable inert diluent or carrier materials, and/or surface active agents. The amount of composition generally applied for the control of nematode pests gives a rate of active ingredient from 0.01 to 10 kg per hectare, preferably from 0.1 to 6 kg per hectare.

The compositions can be applied to the soil, plant or seed, to the locus of the pests, or to the habitat of pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carries and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oil. with the active ingredient. Other additives may also be included, such as emulsifying agents, wetting agents or dispersing agents.

Microencapsulated formulations (microcapsule suspensions CS) or other controlled release formulations may be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogenous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalne sulphonate, and a mixture of the sodium salts of diisopropyl- and triisopropylnaphthalene sulphonates. Suitable agents of the non-ionic type include, for example, the condensation products of ethylene oxide with fatty alcohols such as olely alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of Formula I may also be formulated as powders (dry seed treatment DS or water dispersible powder WS) or liquids (flowable concentrate FS, liquid seed treatment LS, or microcapsule suspension CS) for use in seed treatments.

In use the compositions are applied to the insect pests, to the locus of the pests, to the habitat of the pests, or to growing plants liable to infestation by the pests, by any of the known means of applying pesticidal compositions, for example, by dusting, spraying, or incorporation of granules.

The compound of Formula I may be the sole active ingredient of the composition or they may be admixed with one or more additional active ingredients such as insecticides, synergists, herbicides, fungicides or plant growth regulators where appropriate. Suitable additional active ingredients for inclusion in admixture with a compound of Formula I may be compounds which will broaden the spectrum of activity of the compositions of the invention or increase their persistence in the location of the pest. They may synergise the activity of the compound of Formula I or complement the activity for example by increasing the speed of effect or overcoming repellency. Additionally multi-component mixtures of this type may help to overcome or prevent the development of resistance to individual components. The particular additional active ingredient included will depend upon the intended utility of the mixture and the type of complementary action required. Examples of suitable insecticides include the following a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3furylmethyl-(E)-1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophs, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates ()including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflummuron, or chlorfluazuron;

e) Organic tin compounds such as cyhexatin, fenbutatin oxide, azocyclotin;

f) Macrolides such as avermectins or milbemycins, for example such as abamectin, ivermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents;

k) Imidacloprid.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylron, cyromazine, methoprene, chlorofluazuron and diflubenzuron may also be included in the compositions.

Examples of suitable synergists for use in the compositions include piperonyl butoxide, sesamax, safroxan and dodecyl imidazole. Suitable herbicides, fungicides and plant-growth regulators for inclusion in the compositions will depend upon the intended target and the effect required. An example of rice selective herbicide which can be included is propanil, an example of a plant growth regulator for use in cotton is "Pix", and examples of fungicides for use in rice include blasticides such as blasticidin-S. The ratio of the compounds of Formula I to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The invention is illustrated by the following examples. Examples 1 to 86 illustrate the preparation of a range of compounds of formula (I). Examples 87–104 illustrate formulations suitable for the application of the the compounds of Formula I according to the invention. The following ingredients are referred to by their Registered Trade Marks and have the composition as shown below.

| Registered Trade Mark | Composition |
| --- | --- |
| Synperonic NP8 } | Nonylphenol-ethylene oxide |
| Synperonic NP13 } | condensate |
| Synperonic OP10 } | |
| Aromasol H | Alkylbenzene solvent |
| Solvesso 200 | Inert organic diluent |
| Keltrol | Polysaccharide |

EXAMPLE 1

This example illustrates the preparation of exo-3-(pyrid-3-yl)-endo-3-cyano-8-methyl-8-azabicyclo[3.2.1]octane.

Potassium t-butoxide (22.4 g) was added portion wise to a stirred mixture of tropinone (11.58 g) and tosylmethyl isocyanide (21.2 g) in dimethoxyethane (240 ml) and ethanol (8 ml) at 0° C. under nitrogen at such a rate to maintain the temperature between 0° C. and 10° C. The mixture was then allowed to warm to room temperature and stirred for a further 4 hours. After standing at room temperature for 3 days the mixture was filtered and the solid residue washed with dimethoxyethane. The filtrate was evaporated under reduced pressure and chromatographed [SiO$_2$; dichloromethane:methanol (90:10)] to give exo-3-cyano-8-methyl-8-azabicyclo[3.2.1]octane (9.1 g).

exo-3-Cyano-8-methyl-8-azabicyclo[3.2.1]octane (10.0 g) in tetrahydrofuran (60 ml) was added dropwise to a stirred solution of lithium diisopropylamide [made by adding n-BuLi (29 ml of a 2.5M solution in hexane) to diisopropylamine (10 ml) in tetrahydrofuran (60 ml)] at −25° C. under nitrogen. The mixture was stirred at −25° C. for 20 minutes and then cooled to −78° C. 3-Fluoropyridine (10.0 g) in tetrahydrofuran (60 ml) was then added dropwise. The mixture was then allowed to warm to room temperature over 6 hours. The mixture was then poured into water and extracted with dichloromethane. The combined extracts were washed with brine, dried (MgSO$_4$), evaporated under reduced pressure and chromatographed [SiO$_2$; dichloromethane:methanol (80:20)] to give a yellow oil which crystallised on standing. The solid was washed with hexane and ether, filtered and air-dried to give exo-3-(pyrid-3-yl)-endo-3cyano-8-methyl-8-azabicyclo[3.2.1]octane (8.2 g).

EXAMPLE 2

This example illustrates the preparation of exo-3(pyrid-3-yl)-endo-3-cyano-8-(2-fluoroethyl)-8-azabicyclo[3.2.1]octane.

Vinyl chloroformate (6.0 ml) in tetrahydrofuran (10 ml) was added dropwise to exo-3-(pyrid-3-yl)-endo-3-cyano-8-methyl-8-azabicyclo[3.2.1]octane (4.0 g) in tetrahydrofuran (40 ml) at 0° C. under nitrogen. The mixture was then heated at 70° C. for 4.5 hours. After cooling to room temperature the mixture was filtered and the solid residue washed with ethyl acetate. The combined filtrates were evaporated under reduced pressure and crystallised on standing to give exo-3-(pyrid-3-yl)-endo-3-cyano-8-(vinyloxycarbonyl)-8-azabicyclo[3.2.1]octane (4.1 g).

exo-3-(Pyrid-3-yl)-endo-3-cyano-8-(vinyloxycarbonyl)-8-azabicyclo[3.2.1]octane (3.5 g) and concentrated hydrochloric acid (3 ml) in methanol (25 ml) were refluxed for 6 hours and then allowed to stand at room temperature overnight. After the mixture had been refluxed for a further 4 hours it was allowed to cool to room temperature and then evaporated under reduced pressure. The mixture was then partitioned between 2M sodium hydroxide and ethyl acetate and the aqueous layer was separated and extracted with ethyl acetate. The combined organic fractions were washed with brine, dried (MgSO$_4$) and evaporated under reduced pressure to give exo-3-(pyrid-3-yl)-endo-3-cyano-8-azabicyclo[3.2.1]octane (1.7 g), which crystallised on standing.

exo-3-(Pyrid-3-yl)-endo-3-cyano-8-azabicyclo[3.2.1]octane (0.2 g), 1-bromo-2-fluoroethane (0.21 ml), potassium carbonate (0.14 g) and tetrahydrofuran (6 ml) were heated at 60° C. for 6.5 hours and then allowed to stand at room temperature overnight. 1-Bromo-2-fluoroethane (0.2 ml) was then added and the mixture heated at 60° C. for 6 hours, cooled to room temperature, filtered and evaporated under reduced pressure. Chromatography [SiO$_2$; dichloromethane:methanol (90:10)] gave exo-3-(pyrid-3-yl)-endo-3-cyano-8-(2-fluoroethyl)-8-azabicyclo[3.2.1]octane (0.123 g) m.p. 84.4° C.

EXAMPLE 3

This example illustrates the preparation of exo-3-(3,5-difluorophenyl)-endo-3-cyano-8-methyl-8-azabicyclo[3.2.1]octane.

exo-3-Cyano-8-methyl-8-azabicyclo[3.2.1]octane (13.6 g in tetrahydrofuran (80 ml) was added dropwise to a stirred solution of lithium diisopropylamide [made by adding n-BuLi (40 ml of a 2.5M solution in hexane) to diisopropylamine (14.0 ml) in tetrahydrofuran (80 ml)] at −25° C. under nitrogen. The mixture was stirred at −25° C. for 0.5 hours and then cooled to −78° C. 1,3,5-Trifluorobenzene (12.0 g) in tetrahydrofuran (80 ml) was added dropwise at such a rate to maintain the temperature below −65° C. The mixture was allowed to warm to room temperature overnight and then poured into water and extracted with dichloromethane. The combined extracts were washed with brine, dried (MgSO$_4$) and evaporated under reduced pressure to give a yellow solid. This was recrystallised from diethyl ether to give exo-3-(3,5-difluorophenyl)-endo-3-cyano-8-methyl-8-azabicyclo[3.2.1]octane. The mother liquour from the recrystallisation was chromatographed [SiO$_2$; dichloromethane:methanol (90.10)] to give further exo-3-(3,5-difluorophenyl)-endo-3-cyano-8-methyl-8-azabicyclo[3.2.1]octane (11.2 g in total).

EXAMPLE 4

This example illustrates the preparation of exo-3-(pyrid-3-yl)-endo-3-cyano-8-(prop-1-yl)-8-azabicyclo[3.2.1]octane.

Vinyl chloroformate (2.5 ml) in diethyl ether (15 ml) was added dropwise to a stirred mixture of exo-3-cyano-8-methyl-8-azabicyclo[3.2.1]octane (3.0 g) in diethyl ether (15 ml) at −5° C. under nitrogen. The mixture was then stirred at 0° C. for 0.5 hours and at reflux for 5 hours. After cooling to room temperature the mixture was filtered and the solid residue washed with diethyl ether. The combined filtrates were evaporated under reduced pressure to give exo-3-cyano-8-(vinyloxycarbonyl)-8-azabicyclo[3.2.1] octane (2.93 g).

exo-3-Cyano-8-(vinyloxycarbonyl)-8-azabicyclo[3.2.1]octane (2.9 g), concentrated hydrochloric acid (1 ml) and methanol (30 ml) were refluxed for 4 hours and then allowed to stand at room temperature overnight. Concentrated hydrochloric acid (1 ml) was added and the mixture refluxed for 4 hours. After cooling to room temperature the mixture was evaporated under reduced pressure, dissolved in ethyl acetate and washed with 2M sodium hydroxide and brine, dried (MgSO$_4$) and evaporated under reduced pressure to give exo-3-cyano-8-azabicyclo[3.2.1]octane (1.09 g) as a dark yellow solid.

exo-3-Cyano-8azabicyclo[3.2.1]octane (0.5 g), 1-bromopropane (0.34 ml) and potassium carbonate (1.27 g) were stirred in ethanol (5 ml) at room temperature for 5 hours. 1-Bromopropane (0.17 ml) was then added and the mixture stirred overnight. 1-Bromopropane (0.17 ml) was added and the mixture stirred at room temperature for 6 hours, a further portion of 1-bromopropane (0.17 ml) was added and the mixture allowed to stand at room temperature for 3 days and then refluxed for 0.5 hours. The mixture was then cooled at room temperature, filtered and the filtrate evaporated under reduced pressure. Chromatography [SiO$_2$; dichloromethane:methanol (90:10)] gave exo-3-cyano-8propyl-8-azabicyclo[3.2.1]octane (0.39 g).

exo-3-Cyano-8propyl-8-azabicyclo[3.2.1]octane (0.32 g) in tetrahydrofuran 92 ml) was added dropwise to a stirred solution of lithium diisopropylamide [made by adding n-BuLi (0.8 ml of a 2.5M solution in hexane to diisopropylamine (0.2 ml) in tetrahydrofuran (2 ml)] at −25° C. under nitrogen. The mixture was stirred at −25° C. for 0.5 hours, cooled to −76° C. and 3-fluoropyridine (0.175 g) in tetrahydrofuran (2 ml) was added dropwise. The mixture was stirred at −76° C. for 1 hour and then allowed to warm slowly to room temperature and allowed to stand overnight. The mixture was poured into water, extracted with ethyl acetate (×3) and the combined extracts washed the brine and water, dried (MgSO$_4$) and evaporated under reduced pressure. Chromatography [SiO$_2$; dichloromethane:methanol (95:5)] gave exo-3-(pyrid-3-yl)-endo-3-cyano-8-(prop-1-yl)-8-azabicyclo[3.2.1]octane (0.35 g).

EXAMPLE 5

This example illustrates the preparation of 3-phenyl-3-cyano-8-benzyl-8-azabicyclo[3.2.1]octane.

Sodium hydride (0.75 g of a 55% suspension in oil) was carefully added to benzyl cyanide (0.69 g) and meso-2,5-bis(chloromethyl)-1-benzylpyrrolidine (1.0 g) in N,N-dimethylformamide (30 ml) at 0° C. under nitrogen. The mixture was stirred at room temperature overnight and then poured into ice-cold water and extracted with dichloromethane. The aqueous layer was allowed to stand at room temperature overnight and then filtered and the solid residue washed with water and air dried. The solid product was chromatographed [SiO$_2$; hexane:ethyl acetate (80:20)] to give a 10:1 (exo-phenyl):(endo-phenyl) mixture of 3-phenyl-3-cyano-8-benzyl-8-azabicyclo[3.2.1]octane (0.21 g).

EXAMPLE 6

This example illustrates the preparation of exo-3-(pyrid-3-yl)-endo-3-cyano-8-benzyl-8-azabicyclo[3.2.1]octane Three drops of 5M hydrochloric acid was added to a stirred mixture of 2,5-dimethoxytetrahydrofuran (16.5 g) and water (70 ml). After 10 minutes a mixture of benzylamine (13.6 ml) and 5M hydrochloric acid (30 ml) were added followed by the immediate addition of a mixture of 1,3-acetonedicarboxylic acid (18.2 g) and sodium acetate (10 g) in water (100 ml). After stirring at room temperature for 3 days, during which carbon dioxide was evolved, the mixture was basified to pH8 and extracted with ethyl acetate (×3). The combined extracts were dried (MgSO$_4$) and evaporated under reduced pressure. Chromatography [SiO$_2$; hexane:ethyl acetate] to give 8-benzyl-8-azabicyclo[3.2.1]octan-3-one (11.2 g).

Potassium t-butoxide (2.5 g) was added portion wise to a stirred mixture of 8-benzyl-8-azabicyclo[3.2.1]octan-3-one (2.0 g), tosylmethyl isocyanide (2.36 g) and ethanol (2 ml) in dimethoxyethane (50 ml) at 0° C. under nitrogen. The mixture was stirred at 0° C. for 0.5 hours and then overnight at room temperature. The mixture was then filtered and the solid residue washed with dimethoxyethane. The combined filtrates were evaporated under reduced pressure and chromatographed [SiO$_2$; hexane:ethyl acetate (80:20)] to give 3-cyano-8-benzyl-8-azabicyclo[3.2.1]octane (0.87 g).

3-Cyano-8-benzyl-8-azabicyclo[3.2.1]octane (0.5 g) in tetrahydrofuran (20 ml) was added dropwise to a stirred solution of lithium diisopropylamide [made by adding n-BuLi (1.5 ml of a 1.6M solution in hexane) to diisopropylamine (0.246 g) in tetrahydrofuran (2 ml)] at −25° C. under nitrogen. After 0.5 hours the mixture was cooled to −76° C. and 3-fluoropyridine (0.215 g) in tetrahydrofuran (2 ml) was added. After 2 hours the mixture was allowed to warm room temperature overnight and water then added. The mixture was then extracted with ethyl acetate (×3) and the combined extracts were washed with brine and water, dried (MgSO$_4$) and evaporated under reduced pressure. Chromatography [SiO$_2$; dichloromethane:methanol (95:5)] gave exo-3-(pyrid-3-yl)-endo-3-cyano-8-benzyl-8-azabicyclo[3.2.1]octane (0.245 g which crystallised on standing m.p. 119–120° C.

EXAMPLE 7

This example illustrates the preparation of exo-3-(pyrid-3-yl)-endo-3-cyano-8-(2-methoxyethyl)-8-azabicyclo[3.2.1]octane.

exo-3-(Pyrid-3-yl)-endo-3-cyano-8-azabicyclo[3.2.1]octane (0.30 g), 2-bromoethyl methyl ether (0.235 g) and potassium carbonate (0.213 g) were refluxed in ethanol (3 ml) for 30 hours. The mixture was allowed to cool to room temperature, filtered and washed with ethanol. The filtrate was evaporated under reduced pressure and chromatographed [SiO$_2$; dichloromethane:methanol (95:5)] to give exo-3-(pyrid-3-yl)-endo-3-cyano-8-(2-methoxyethyl)-8-azabicyclo[3.2.1]octane (0.223 g).

EXAMPLE 8

This example illustrates the preparation of exo-3-(pyrid-2-yl)-endo-3-cyano-8-methyl-8-azabicyclo[3.2.1]octane.

exo-3-Cyano-8-methyl-8-azabicyclo[3.2.1]octane (0.5 g) in tetrahydrofuran (3 ml) was added to a solution of lithium diisopropylamide [made by adding n-BuLi (1.6 ml of a 2.5M solution in hexane) to diisopropylamine (0.4 g) in tetrahydrofuran (3 ml)] at −25° C. under nitrogen. After 30 minutes a solution of 2-fluoropyridine (0.388 g) in tetrahydrofuran (3 ml) was added. After 1 hour the mixture was allowed to warm to room temperature and then stand overnight. Water was added and the mixture extracted with ethyl acetate (×3). The combined extracts were washed with water (×2), dried (MgSO$_4$) and evaporated under reduced pressure. Chromatography [SiO$_2$; dichloromethane:methanol (90:10)] gave exo-3-(pyrid-2-yl)-endo-3-cyano-8-methyl-8-azabicyclo[3.2.1]octane (0.467 g).

EXAMPLE 9

This example illustrates the preparation of exo-3-(pyrazin-2-yl)-endo-3-cyano-8-methyl-8-azabicyclo[3.2.1]octane.

exo-3-Cyano-8-methyl-8-azabicyclo[3.2.1]octane (0.5 g) in tetrahydrofuran (3 ml) was added to a solution of lithium diisopropylamide [made by adding n-BuLi (1.6 ml of a 2.5M solution in hexane) to diisopropylamine (0.4 g) in tetrahydrofuran (3 ml)] at −25° C. under nitrogen. After 30 minutes the mixture was cooled to −78° C. and a solution of chloropyrazine (0.46 g) in tetrahydrofuran (5 ml) was added. After 1 hour the mixture was allowed to warm to room temperature and stand overnight. Water was added and the mixture extracted with ethyl acetate (×3). The combined extracts were washed with brine and water, dried (MgSO$_4$) and evaporated under reduced pressure. Chromatography [SiO$_2$; dichloromethane:methanol (95:5) to (90:10)] gave exo-3-(pyrazin-2-yl)-endo-3-cyano-8-methyl-8-azabicyclo[3.2.1]octane (0.368 g) m.p. 76–77° C.

EXAMPLE 10

This example illustrates the preparation of exo-3-(6-chloropyrazin-2-yl)-endo-3-cyano-8-methyl-8-azabicyclo[3.2.1]octane.

exo-3-Cyano-8-methyl-8-azabicyclo[3.2.1]octane (1.0 g) in tetrahydrofuran (5 ml) was added to a solution of lithium diisopropylamide [made by adding n-BuLi (2.66 ml of a 2.5M solution in hexane) to diisopropylamine (0.673 g) in tetrahydrofuran (5 ml)] at −25° C. under nitrogen. After 30 minutes the mixture was cooled to −78° C. and a solution of 2,6-dichloropyrazine (1.0 g) in tetrahydrofuran (5 ml) was added. After 1 hour the mixture was allowed to warm to room temperature and stand over the weekend. Water was added and the mixture extracted with ethyl acetate (×3). The combined extracts were washed with brine and water, dried (MgSO$_4$) and evaporated under reduced pressure. Chromatography [SiO$_2$; dichloromethane:methanol (95:5)] gave exo-3-(6-chloropyrazin-2-yl)-endo-3-cyano-8-methyl-8-azabicyclo[3.2.1]octane (1.10 g) m.p. 79.8–80.1° C.

EXAMPLE 11

This example illustrates the preparation of exo-3-(6-chloropyridazin-3-yl)-endo-3-cyano-8-methyl-8-azabicyclo[3.2.1]octane.

exo-3-Cyano-8-methyl-8-azabicyclo[3.2.1]octane (0.5 g) in tetrahydrofuran (5 ml) was added to a solution of lithium diisopropylamide [made by adding n-BuLi (1.4 ml of a 2.5M solution in hexane) to diisopropylamine (0.45 g) in tetrahydrofuran (2 ml)] at −25° C. under nitrogen. After 30 minutes 1,3-dimethylimidazolidinone (1 ml) was added and the mixture cooled to −78° C. A solution of 3,6-dichlorochloropyridazine (0.50 g) in tetrahydrofuran (2 ml) was added. After 2 hours the mixture was allowed to warm to room temperature and stand overnight. Water was added and the mixture extracted with ethyl acetate (×3). The combined extracts were washed with brine and water, dried (MgSO$_4$) and evaporated under reduced pressure. Chromatography [SiO$_2$; dichloromethane:methanol (95:5)] gave exo-3-(6-chloropyridazin-3-yl)-endo-3-cyano-8-methyl-8azabicyclo[3.2.1]octane (0.082 g).

EXAMPLE 12

This example illustrates the preparation of exo-3-(5,6-dichloropyrid-3-yl)-endo-3-cyano-8-methyl-8-azabicyclo[3.2.1]octane.

3-Chloro-2-hydroxy-5-nitropyridine (4.8 g) was added to phosphorus oxychloride (11 ml) and phosphorus pentachloride (4.45 g) and the mixture refluxed overnight. The mixture was then cooled to room temperature and evaporated under reduced pressure. Iced water was added to the mixture and a solid product formed. The solid was removed by filtration, washed with water and air-dried to give 2,3-dichloro-5-nitropyridine (3.94 g).

2,3-Dichloro-5-nitropyridine (3.9 g) and iron powder (3.0 g) were added to isopropyl alcohol (40 ml) and water (8 ml) and the mixture refluxed for 4 hours. The mixture was then cooled to room temperature and filtered (celite). The filtrate was evaporated under reduced pressure and chromatographed [SiO$_2$; hexane:ethyl acetate (80:20) to (50:50)] to give 5-amino-2,3-dichloropyridine (1.71 g).

5-Amino-2,3-dichloropyridine (0.80 g) in dichloromethane (10 ml) was added to known trifluoride etherate (0.92 ml) at −15° C. under nitrogen. Dichloromethane (15 ml) was added followed by t-butylnitrite (0.71 ml) in dichloromethane (5 ml). After 15 minutes the mixture was allowed to warm to −5° C. over 20 minutes. Hexane was added and the resulting solid was filtered, air-dried and washed with ether and stored at approximately −20° C. overnight. The solid was then heated until gas evolution had ceased and the product kugelrohr distilled to give 2,3-dichloro-5-fluoropyridine (0.104 g).

exo-3-Cyano-8-methyl-8-azabicyclo[3.2.1]octane (0.10 g) in tetrahydrofuran (1 ml) was added to a solution of lithium diisopropylamide [made by adding n-BuLi (0.29 ml of a 2.5M solution in hexane) to diisopropylamine (0.073 g) in tetrahydrofuran (1 ml)] at −25° C. under nitrogen. After 30 minutes, 2,3-dichloro-5-fluoropyridine (0.10 g) in tetrahydrofuran (1 ml) was added. After 1 hour the mixture was allowed to warm to room temperature and stand overnight. Water was added and the resulting mixture extracted with ethyl acetate (×3). The combined extracts were washed with water, dried (MgSO$_4$) and evaporated under reduced pressure. Chromatography [SiO$_2$; dichloromethane:methanol (95:5) to (90:10)] gave an orange gum which was triturated with hexane to give exo-3-(5,6-dichloropyrid-3-yl)-endo-3-cyano-8methyl-8-azabicyclo[3.2.1]octane (0.019 g) as a yellow solid.

EXAMPLE 13

This example illustrates the preparation of exo-3-(pyrid-3-yl)-endo-3-cyano-8-(methoxycarbonylmethyl)-8-azabicyclo[3.2.1]octane.

exo-3-(Pyrid-3-yl)-endo-3-cyano-8-azabicyclo[3.2.1]octane (0.20 g), ethyl bromoacetate (0.187 g) and potassium carbonate (0.155 g) were refluxed in ethanol (3 ml) for 4 hours. The mixture was then filtered and the filtrate evaporated under reduced pressure. Chromatography [SiO$_2$; dichloromethane:methanol (95:5)] gave exo-3-(pyrid-3-yl)-endo-3-cyano-8-(methoxycarbonylmethyl)-8-azabicyclo[3.2.1]octane (0.112 g).

EXAMPLE 14

This example illustrates the preparation of exo-3-(pyrid-3-yl)-endo-3-cyano-8-(methylsulphonylmethylsulphonyl)-8-azabicyclo[3.2.1]octane.

exo-3-(Pyrid-3-yl)-endo-3-cyano-8azabicyclo[3.2.1]octane (0.39 g) and triethylamine (15 ml) were added to dichloromethane (5ml) and the mixture cooled to −20° C. Methane sulphonyl chloride (0.12 ml) was added dropwise and the mixture allowed to warm to room temperature. After 1 hour the mixture was evaporated under reduced pressure and dissolved in ethyl acetate. The resulting solution was washed with aqueous sodium bicarbonate solution and water (×2), dried (MgSO$_4$) and evaporated under reduced pressure. Chromatography [SiO$_2$; dichloromethane:methanol (90:10)] gave a gum which formed a solid on trituration with hexane and ether. Chromatography [SiO$_2$; hexane:ethyl acetate (80:20)] gave exo-3-(pyrid-3-yl)-endo-3-cyano-8-(methylsulphonylmethylsulphonyl)-8-azabicyclo[3.2.1]octane (0.028 g) m.p. 163–164° C.

EXAMPLE 15

This example illustrates the preparation of exo-3-(6-chloropyrid-3-yl)-endo-3-cyano-8-methyl-8-azabicyclo[3.2.1]octane.

exo-3-(Pyrid-3-yl)-endo-3-cyano-8-azabicyclo[3.2.1]octane (0.50 g) in acetonitrile (3 ml) was added dropwise to a stirred solution of di-t-butyl carbonate (0.512 g) in acetonitrile (5 ml) at 0° C. 4-Dimethylaminopyridine (0.02 g) was added and after 30 minutes the mixture was warmed to room temperature, stirred for 2 hours and allowed to stand overnight. The mixture was evaporated under reduced pressure and chromatographed [SiO$_2$; ethyl acetate:dichloromethane (20:80) to (30:70)] to give exo-3-(pyrid-3-yl)-endo-3-cyano-8-(t-butyloxycarbonyl)-8-azabicyclo[3.2.1]octane (0.602 g).

m-Chloroperoxybenzoic acid (0.22 g) was added to a solution of exo-3-(pyrid-3-yl)-endo-3-cyano-8-(t-butyloxycarbonyl)-8-azabicyclo[3.2.1]octane (0.20 g) in dichloromethane (2 ml) at 0° C. under nitrogen. After 1 hour the mixture was warmed to room temperature and allowed to stand overnight. The mixture was evaporated under reduced pressure, dissolved in ethyl acetate, washed with aqueous sodium bicarbonate solution (×2), dried (MgSO$_4$) and evaporated under reduced pressure to give exo-3-(N-oxopyrid-3-yl)-endo-3-cyano-8-(t-butyloxycarbonyl)-8-azabicyclo[3.2.1]octane (0.161 g).

exo-3-(N-oxopyrid-3-yl)-endo-3-cyano-8-(t-butyloxycarbonyl)-8-azabicyclo[3.2.1]octane (0.161 g) was added to phosphorus oxychloride (1 ml) and the mixture refluxed for 1 hour. The mixture was then allowed to cool to room temperature, evaporated under reduced pressure, toluene added and evaporated under reduced pressure. Ethyl acetate was added and the mixture was washed with aqueous sodium hydroxide solution and water (×2), dried (MgSO$_4$) and evaporated under reduced pressure to give exo-3-(6-chloropyrid-3-yl)-endo-3-cyano-8-azabicyclo[3.2.1]octane (0.058 g).

exo-3-(6-Chloropyrid-3-yl)-endo-3-cyano-8-azabicyclo[3.2.1]octane (0.05 g) and paraformaldehyde (0.50 g) were added to formic acid (2 ml) and the mixture heated under reflux. After 2 hours the mixture was allowed to cool to room temperature and stand overnight. The mixture was evaporated under reduced pressure and 2M sodium hydroxide added. The mixture was extracted with ethyl acetate (×3) and the combined extracts were washed with brine and water, dried (MgSO$_4$), evaporated under reduced pressure and chromatographed [SiO$_2$; dichloromethane:methanol (95:5)] to give exo-3-(6-chloropyrid-3-yl)-endo-3-cyano-8-methyl-8-azabicyclo[3.2.1]octane (0.023 g).

EXAMPLE 16

This example illustrates the preparation of exo-3-(5-chloropyrid-3-yl)-endo-3-cyano-8-(n-hexyl)-8-azabicyclo[3.2.1]octane.

exo-3-Cyano-8-methyl-8-azabicyclo[3.2.1]octane (0.5 g) in tetrahydrofuran (3 ml) was added to a solution of lithium diisopropylamide [made by adding n-BuLi (1.6 ml of a 2.5M solution in hexane) to diisopropylamine (0.4 g) in tetrahydrofuran (3 ml] at −25° C. under nitrogen. After a further 15 minutes at −25° C. 3,5-dichloropyridine (0.588 g) in tetrahydrofuran (3 ml) was added at −78° C. After 1 hour at the mixture was allowed to warm to room temperature and stand overnight. Water was then added and the resulting mixture extracted with ethyl acetate (×3). The combined extracts were washed with brine and water, dried (MgSO$_4$) and evaporated under reduced pressure. Chromatography [SiO$_2$; dichloromethane:methanol (90:10)] gave exo-3-(5-chloropyrid-3-yl)-endo-3-cyano-8-methyl-8-azabicyclo[3.2.1]octane. (0.249 g)

Vinyl chloroformate (2.6 ml) in tetrahydrofuran (5 ml) was added to a stirred solution of exo-3-(5-chloropyrid-3-yl)-endo-3-cyano-8-methyl-8-azabicyclo[3.2.1]octane (2.6 g) in tetrahydrofuran (25 ml) at 0° C. The mixture was allowed to warm to room temperature over 1 hour, refluxed for 2 hours and then allowed to cool to room temperature. After 20 hours the mixture was partitioned between water and ethyl acetate and the organic layer was separated, washed with water and dried (MgSO$_4$). Evaporation under reduced pressure gave exo-3-(5-chloropyrid-3-yl)-endo-3-cyano-8-(vinyloxycarbonyl)-8-azabicyclo[3.2.1]octane (2.0 g).

exo-3-(5-Chloropyrid-3-yl)-endo-3-cyano-8-(vinyloxycarbonyl)-8-azabicyclo[3.2.1]octane (2.6 g) was dissolved in methanol (50 ml) and concentrated hydrochloric acid (7 ml) added. The mixture was refluxed for 3 hours after which the mixture was evaporated under reduced pressure and basified with aqueous sodium carbonate. The resulting mixture was extracted with ethyl acetate and evaporated under reduced pressure to give a brown solid. This was then washed with hexane to give exo-3-(5-chloropyrid-3-yl)-endo-3-cyano-8-azabicyclo[3.2.1]octane (1.2 g).

n-Hexyl bromide (0.1 ml) and potassium carbonate (0.1 g) were added to exo-3-(5-chloropyrid-3-yl)-endo-3-cyano-8-azabicyclo[3.2.1]octane (0.15 g) in ethanol (2 ml) and the mixture refluxed for 44 hours. The mixture was then diluted with ethanol, filtered and evaporated under reduced pressure. Chromatography [SiO$_2$; dichloromethane:methanol (96:4)] gave exo-3-(5-chloropyrid-3-yl)-endo-3-cyano-8-(n-hexyl)-8-azabicyclo[3.2.1]octane (0.123 g).

EXAMPLE 17

This example illustrates the preparation of exo-3-(5-chloropyrid-3-yl)-endo-3-cyano-8-allyl-8-azabicyclo[3.2.1]octane.

Allyl bromide (62 µl) and potassium carbonate (0.1 g) were added to exo-3-(5-chloropyrid-3-yl)-endo-3-cyano-8-azabicyclo[3.2.1]octane (0.15 g) in ethanol (2 ml) and the mixture stirred for 3 hours and then allowed to stand overnight. The mixture was diluted with ethanol, filtered and evaporated under reduced pressure. Chromatography [SiO$_2$; dichloromethane:methanol (95:5)] gave exo-3-(5-chloropyrid-3-yl)-endo-3-cyano-8-allyl-8-azabicyclo[3.2.1]octane (0.167 g).

EXAMPLE 18

This example illustrated the preparation of exo-3-(5-chloropyrid-3-yl)-endo-3-cyano-8-(2,2,2-trifluoroethyl)-8-azabicyclo[3.2.1]octane.

A few drops of dilute hydrochloric acid were added to a solution of 2,5-dimethoxytetrahydrofuran (16.5 g) in water (70 ml). After stirring at room temperature for 30 minutes 2,2,2-trifluoroethylamine hydrochloride (16.9 g), 1,3-acetonedicarboxylic acid (18.3 g) and sodium acetate (10.0 g) were added and the mixture stirred at room temperature for 2 days. The mixture was diluted to 500 ml with water, saturated with potassium carbonate and extracted with ethyl acetate (×2). The combined organic extracts were washed with aqueous potassium carbonate, dried (MgSO$_4$) and evaporated under reduced pressure. Distillation (90° C.; 0.1 mmHg) gave 8-(2,2,2-trifluoroethyl)-8-azabicyclo[3.2.1]octan-3-one (8.7 g).

Potassium t-butoxide (5.4 g) was added slowly with cooling to a stirred solution of 8-(2,2,2-trifluoroethyl)-8-azabicyclo[3.2.1]octan-3-one (4.0 g) and tosylmethyl isocyanide (4.9 g) in dimethoxyethane (80 ml) and ethanol (5 ml) under nitrogen at such a rate so as to keep the temperature below 10° C. The mixture was stirred for 18 hours while allowing it to warm to room temperature, evaporated under reduced pressure and added to aqueous potassium carbonate solution. The mixture was extracted with ethyl acetate (×2) and the combined extracts were dried (MgSO$_4$) and evaporated under reduced pressure to give an oil. The mixture was extracted with refluxing hexane and the extracts allowed to cool and evaporated under reduced pressure to give exo-3-cyano-8-(2,2,2-trifluoroethyl)-8-azabicyclo[3.2.1]octane (2.5 g) m.p. 90–92° C.

exo-3-Cyano-8-(2,2,2-trifluoroethyl)-8-azabicyclo[3.2.1]octane (1.09 g) in tetrahydrofuran (10 ml) was added to a stirred solution of lithium diisopropylamide [made by adding n-BuLi (2.4 ml of a 2.5M solution in hexane) to diisopropylamine (0.61 g) in tetrahydrofuran (10 ml)] at −25° C. under nitrogen. After 2 hours at −25° C. the mixture was cooled to −76° C. and 3,5-dichloropyridine (0.74 g) in tetrahydrofuran (10 ml) added. The mixture was allowed to warm to room temperature, stirred for 18 hours and evaporated under reduced pressure. The mixture was dissolved in ether, washed with water (×2), dried ($MgSO_4$) and evaporated under reduced pressure. Chromatography [$SiO_2$; diethyl ether:hexane (20:80) to (50:50)] gave exo-3-(5-chloropyrid-3-yl)-endo-3-cyano-8-(2,2,2-trifluoroethyl)-8-azabicyclo[3.2.1]octane (0.45 g) m.p. 109.5–111.5° C.

EXAMPLE 19

This example illustrated the preparation of exo-3-(5-bromopyrid-3-yl)-endo-3-cyano-8-methyl-8-azabicyclo[3.2.1]octane.

exo-3-Cyano-8-azabicyclo[3.2.1]octane (0.5 g) in tetrahydrofuran (3 ml) was added to a solution of lithium diisopropylamide [made by adding n-BuLi (1.6 ml of a 2.5 M solution in hexane) to diisopropylamine (0.4 g) in tetrahydrofuran (3 ml)] at −25° C. under nitrogen. After 30 minutes the mixture was cooled to −76° C. and a solution of 3,5-dibromopyridine (0.94 g) in tetrahydrofuran (3 ml) added. After 1 hour the mixture was allowed to warm to room temperature and left to stand overnight. Water was added and the resulting mixture extracted with ethyl acetate (×3). The combined extracts were washed with brine (×2) and water, dried ($MgSO_4$) and evaporated under reduced pressure. Chromatography [$SiO_2$; dichloromethane:methanol (90:10)] gave exo-3-(5-bromopyrid-3-yl)-endo-3-cyano-8-methyl-8-azabicyclo[3.2.1]octane (0.327 g) m.p. 144–145° C.

EXAMPLE 20

This example illustrates the preparation of exo-3-(5-cyanopyrid-3-yl)-endo-3-cyano-8-methyl-8-azabicyclo[3.2.1]octane.

exo-3-(5-Bromopyrid-3-yl)-endo-3-cyano-8-methyl-8-azabicyclo[3.2.1]octane (0.30 g) and copper(I) cyanide (0.345 g) were heated at 200° C. in N-methylpyrrolidinone (10 ml) under nitrogen. After 36 hours the reaction was allowed to cool to room temperature and water was added followed by aqueous ammonium hydroxide solution (density=0.88). The mixture was extracted with ethyl acetate (×3) and the combined extracts were washed with brine and water, dried ($MgSO_4$) and evaporated under reduced pressure. The resulting oil was dissolved in ether and washed with brine (×7), dried ($MgSO_4$) and evaporated under reduced pressure. Chromatography [$SiO_2$; dichloromethane:methanol (95:5)] gave a yellow solid. This was recrystallised three times (from dichloromethane/hexane, ethyl acetate/hexane and dichloromethane/hexane) to give exo-3-(5-cyanopyrid-3-yl)-endo-3-cyano-8-methyl-8-azabicyclo[3.2.1]octane (0.49 g) m.p. 183.5–184° C.

EXAMPLE 21

This example illustrates the preparation of exo-3-(5-ethoxypyrid-3-yl)-endo-3-cyano-8-methyl-8-azabicyclo[3.2.1]octane.

exo-3-(5-Chloropyrid-3-yl)-endo-3-cyano-8-methyl-8-azabicyclo[3.2.1]octane (0.30 g) and sodium ethoxide (0.625 g) were heated at 80° C. in N,N-dimethylformamide (10 ml) under nitrogen. After 5 hours the mixture was allowed to cool to room temperature and water added. The mixture was extracted with ethyl acetate (×3) and the combined extracts were washed with brine (×2) and water, dried ($MgSO_4$) and evaporated under reduced pressure. Chromatography [$SiO_2$; dichloromethane:methanol (90:10)] gave an oil. A small amount of hexane was added and the mixture was allowed to stand at approximately 0° C. overnight after which a solid product had formed. The mixture was filtered and the solid washed with a small amount of hexane to give exo-3-(5-ethoxypyrid-3-yl)-endo-3-cyano-8-methyl-8-azabicyclo[3.2.1]octane (0.105 g) m.p. 56–57° C.

EXAMPLE 22

This example illustrates the preparation of exo-3-(5-chloropyrid-3-yl)-endo-3-cyano-8-isopropyl-8-azabicyclo[3.2.1]octane.

2M Hydrochloric acid (8 drops) was added to a stirred solution of 2,5-dimethoxytetrahydrofuran (16.5 g) in water (70 ml). After 15 minutes a mixture of diisopropylamine (7.38 g) and 2M hydrochloric acid (40 ml) was added to the reaction followed by acetonedicarboxylic acid (18.25 g) and sodium acetate (10.0 g) in water (100 ml). After 3 days 1,3-acetonedicarboxylic acid (6.0 g) and sodium acetate (3.0 g) were added. After a further 6 days the mixture was basified to pH8 and extracted with ethyl acetate. The extracts were dried ($MgSO_4$) and evaporated under reduced pressure. The aqueous fraction was then extracted with chloroform and the extracts dried ($MgSO_4$) and evaporated under reduced pressure. Distillation of the combined extracts (95–115° C.; 18 mmHg) gave, 8-isopropyl-8-azabicyclo[3.2.1]octan-3-one (3.37 g).

Potassium t-butoxide (5.0 g) was added slowly with cooling to a stirred solution of 8-isopropyl-8-azabicyclo[3.2.1]octan-3-one (3.16 g) and tosylmethyl isocyanide (4.80 g) in dimethoxyethane (50 ml) and ethanol (2.2 ml) under nitrogen at such a rate so as to keep the temperature below 10° C. After 1 day tosylmethyl isocyanide (1.0 g), potassium t-butoxide (1.0 g) and ethanol (1 ml) were added. After a further day the mixture was filtered and the filtrate evaporated under reduced pressure and chromatographed [$SiO_2$; dichloromethane:methanol (95:5)] to give exo-3-cyano-8-isopropyl-8-azabicyclo[3.2.1]octane (0.90 g).

Lithium bis(trimethylsilyl)amide (2.5 ml of a 1M solution in tetrahydrofuran) in tetrahydrofuran (5 ml) was added to a stirred solution of exo-3-cyano-8-isopropyl-8-azabicyclo[3.2.1]octane (0.38 g) and 3,5-dichloropyridine (0.34 g) in tetrahydrofuran (5 ml) at 10° C. over 30 minutes. The mixture was then stirred at room temperature for 2 hours and allowed to stand at room temperature overnight. 3,5-Dichloropyridine (0.15 g) was added followed by lithium bis(trimethylsilyl)amide (1.0 ml of a 1M solution in tetrahydrofuran) over 30 minutes. After 2 hours lithium bis(trimethylsilyl)amide (1.0 ml of a 1M solution in tetrahydrofuran) was added dropwise and after a further 1 hour additional lithium bis(trimethylsilyl)amide (1.0 ml of a 1M solution in tetrahydrofuran) was added and the mixture warmed to 50° C. After 5 minutes the reaction was cooled to room temperature and aqueous sodium carbonate solution added. The mixture was extracted with ethyl acetate (×2) and the combined extracts washed with brine, dried ($MgSO_4$) and evaporated under reduced pressure to give a brown oil. The oil was extracted with boiling hexane and the combined extracts evaporated under reduced pressure to give exo-3-(5-chloropyrid-3-yl)-endo-3-cyano-8-isopropyl-8-azabicyclo[3.2.1]octane (0.60 g).

EXAMPLE 23

This example illustrates the preparation of exo-3-(2,6-dichloropyrimid-4-yl)-endo-3-cyano-8-methyl-8-azabicyclo[3.2.1]octane.

exo-3-Cyano-8-methyl-8-azabicyclo[3.2.1]octane (0.5 g) in tetrahydrofuran (3 ml) was added to a solution of lithium diisopropylamide [made by adding n-BuLi (1.6 ml of a 2.5 M solution in hexane) to diisopropylamine (0.4 g) in tetrahydrofuran (3 ml)] at −25° C. under nitrogen. After 30 minutes the mixture was cooled to −78° C. and a solution of 2,4,6-trichloropyrimidine (0.728 g) in tetrahydrofuran (5 ml) was added. After 1 hour the mixture was allowed to warm to room temperature, stirred for 2 hours and allowed to stand overnight. Water was added and the mixture extracted with ethyl acetate (×3). The combined extracts were washed with brine and water, dried ($MgSO_4$) and evaporated under reduced pressure. Chromatography [$SiO_2$; dichloromethane:methanol (95:5) to (90:10)] gave exo-3-(2,6-dichloropyrimid-4-yl)-endo-3-cyano-8-methyl-8-azabicyclo[3.2.1]octane (0.087 g) m.p. 95–97° C.

EXAMPLE 24

This example illustrates the preparation of exo-3-(2-chloropyrid-4-yl)-endo-3-cyano-8-methyl-8-azabicyclo[3.2.1]octane.

exo-3-Cyano-8-methyl-8-azabicyclo[3.2.1]octane (0.5 g) in tetrahydrofuran (3 ml) was added to a solution of lithium diisopropylamide [made by adding n-BuLi (1.6 ml of a 2.5 M solution in hexane) to diisopropylamine (0.4 g) in tetrahydrofuran (3 ml)] at −25° C. under nitrogen. After 30 minutes the mixture was cooled to −78° C. and a solution of 2,4,6-trichloropyridine (0.724 g) in tetrahydrofuran (5 ml) was added. After 1 hour the mixture was allowed to warm to room temperature and allowed to stand overnight. Water was added and the mixture extracted with ethyl acetate (×3). The combined extracts were dried ($MgSO_4$) and evaporated under reduced pressure. Chromatography [$SiO_2$; dichloromethane:methanol (95:5)] gave a solid product which was recrystallised (ethyl acetate/hexane) to give exo-3-(2,6-dichloropyrid-4-yl)-endo-3-cyano-8-methyl-8-azabicyclo[3.2.1]octane (0.389 g) m.p. 165–166° C.

exo-3-(2,6-Dichloropyrid-4-yl)-endo-3-cyano-8-methyl-8-azabicyclo[3.2.1]octane (0.50 g) and hydrazine hydrate (0.106 ml) were refluxed in isopropyl alcohol (5 ml) for 5 hours and then left to stand overnight. Hydrazine hydrate (0.106 ml) was added and the mixture refluxed for 8 hours. More hydrazine hydrate (0.106 ml) was added and the mixture refluxed for a further 8 hours. After cooling to room temperature the mixture was evaporated under reduced pressure and the residue extracted with dichloromethane. The extracts washed with water (×2), dried ($MgSO_4$), evaporated under reduced pressure and triturated with hexane and ether to give exo-3-(2-chloro-6-hydrazinopyrid-4-yl)-endo-3-cyano-8-methyl-8-azabicyclo[3.2.1]octane (0.205 g) m.p. 215–216° C.

Copper(II) sulphate octahydrate (0.36 g) was added to a solution of exo-3-(2-chloro-6-hydrazinopyrid-4-yl)-endo-3-cyano-8-methyl-8-azabicyclo[3.2.1]octane (0.170 g) in water (3 ml) and the mixture refluxed for 7 hours. After cooling to room temperature ammonium hydroxide solution (density=0.88) was added and the mixture extracted with ethyl acetate (×3). The combined extracts were washed with brine and water, dried ($MgSO_4$) and evaporated under reduced pressure. Chromatography [$SiO_2$; dichloromethane:methanol (90:10)] gave exo-3-(2-chloropyrid-4-yl)-endo-3-cyano-8-methyl-8-azabicyclo[3.2.1]octane (0.052 g) m.p. 104–105° C.

EXAMPLE 25

This example illustrates the preparation of exo-3-(pyrid-4-yl)-endo-3-cyano-8-methyl-8-azabicyclo[3.2.1]octane.

exo-3-(2,6-Dichloropyrid-4-yl)-endo-3-cyano-8-methyl-8-azabicyclo[3.2.1]octane (0.35 g), crushed potassium hydroxide (0.133 g) and palladium on charcoal (0.20 g) were stirred in methanol (10 ml) under hydrogen for 3 hours and then allowed to stand for 3 days. The mixture was filtered (celite), evaporated under reduced pressure and dissolved in ethyl acetate. The resulting solution was washed with aqueous sodium hydroxide and water, dried ($MgSO_4$) and evaporated under reduced pressure to give a solid product which was washed with hexane and ether to give exo-3-(pyrid-4-yl)-endo-3-cyano-8-methyl-8-azabicyclo[3.2.1]octane (0.072 g) m.p. 74.5–76° C.

EXAMPLE 26

This example illustrates the preparation of exo-3-(5-chloropyrid-3-yl)-endo-3-cyano-8-(3,3-difluoroprop-2-en-1-yl)-8-azabicyclo[3.2.1]octane.

exo-3-(5-Chloropyrid-3-yl)-endo-3-cyano-8-azabicyclo[3.2.1]octane (0.248 g), 1-bromo-1,1-difluoroprop-2-ene (0.314 g) and potassium carbonate (0.345 g) were stirred in ethanol (2 ml) for 2 hours and then allowed to stand for 4 days. The mixture was then evaporated under reduced pressure and water added. The mixture was then extracted with dichloromethane (×3) and the combined extracts were washed with brine, dried ($MgSO_4$) and evaporated under reduced pressure. Filtration [$SiO_2$; dichloromethane:methanol (98:2)] gave exo-3-(5-chloropyrid-3-yl)-endo-3-cyano-8-(3,3-difluoroprop-2-en-1-yl)-8-azabicyclo[3.2.1]octane (0.287 g).

EXAMPLE 27

This example illustrates the preparation of exo-3-(5-chloropyrid-3-yl)-endo-3-cyano-8-(3-oxo-4,4,4-trifluorobut-1-en-1-yl)-8-azabicyclo[3.2.1]octane.

exo-3-(5-Chloropyrid-3-yl)-endo-3-cyano-8-azabicyclo[3.2.1]octane (0.30 g), 4-ethoxy-1,1,1-trifluorobut-3-en-2-one (0.204 g) and potassium carbonate (0.20 g) were heated under reflux in ethanol. After 4 hours the mixture was allowed to cool to room temperature and water added. The mixture was extracted with ethyl acetate (×3) and the combined extracts were washed with brine (×2) and water, dried ($MgSO_4$) and evaporated under reduced pressure. Chromatography [$SiO_2$; dichloromethane:methanol (95:5)] gave exo-3-(5-chloropyrid-3-yl)-endo-3-cyano-8-(3-oxo-4,4,4-trifluorobut-1-en-1-yl)-8-azabicyclo[3.2.1]octane (0.162 g) m.p. 144–145° C.

EXAMPLE 28

This example illustrates the preparation of exo-3-(5-chloropyrid-3-yl)-endo-3-cyano-8-acetyl-8-azabicyclo[3.2.1]octane.

N,N-Diisopropylethylamine (0.43 ml) and acetyl chloride (0.18 ml) were added to exo-3-(5-chloropyrid-3-yl)-endo-3-cyano-8-azabicyclo[3.2.1]octane (0.50 g) in dichloromethane (10 ml) at room temperature. After 10 minutes the mixture was evaporated under reduced pressure and ethyl acetate (50 ml) added. The resulting mixture was washed with potassium carbonate solution, dried ($MgSO_4$) and evaporated under reduced pressure. The resulting product was triturated with hot hexane and evaporated under reduced pressure to give exo-3-(5-chloropyrid-3-yl)-endo-3-cyano-8-acetyl-8-azabicyclo[3.2.1]octane (0.43 g) m.p. 162–165° C.

EXAMPLE 29

This example illustrates the preparation of exo-3-(5-chloropyrid-3-yl)-endo-3-cyano-8-azabicyclo[3.2.1]octane hydroperchlorate.

Perchloric acid (1.19 ml) was added dropwise to a stirred suspension of exo-3-(5-chloropyrid-3-yl)-endo-3-cyano-8-azabicyclo[3.2.1]octane (5.0 g) in diethyl ether (100 ml) at room temperature. After 5 hours the mixture was filtered and the precipitate washed with diethyl ether to give exo-3-(5-chloropyrid-3-yl)-endo-3-cyano-8-azabicyclo[3.2.1]octane hydroperchlorate (5.36 g).

EXAMPLE 30

This example illustrates the preparation of exo-3-(5-chloropyrid-3-yl)-endo-3-cyano-8-(tert-butyl)-8-azabicyclo[3.2.1]octane.

Acetone (0.42 ml) was added to a stirred solution of exo-3-(5-chloropyrid-3-yl)-endo-3-cyano-8-azabicyclo[3.2.1]octane hydroperchlorate (1.0 g) in ethanol (2 ml) at room temperature under nitrogen. After 30 minutes the mixture was heated to 50° C. After 1 hour the mixture was evaporated under reduced pressure. Acetone was then added and the mixture heated under reflux for 3 hours and then evaporated under reduced pressure. Diethyl ether (10 ml) was added followed by methylmagnesium bromide (4.3 ml of a 3.0M solution in diethyl ether). The mixture was then heated under reflux for 6 hours and then allowed to stand at room temperature overnight. Saturated ammonium chloride solution was then added and the mixture extracted with dichloromethane (×3). The combined extracts were washed with brine, dried (MgSO$_4$) and evaporated under reduced pressure. Chromatography [SiO$_2$; dichloromethane:methanol (95:5)] gave exo-3-(5-chloropyrid-3-yl)-endo-3-cyano-8-(tert-butyl)-8-azabicyclo[3.2.1]octane (0.218 g) m.p. 127–129° C.

EXAMPLE 31

This example illustrates the preparation of exo-3-(5-chloropyrid-3-yl)-endo-3-cyano-8-(2-phenyl-3-oxo-prop-2-yl)-8-azabicyclo[3.2.1]octane.

2-Phenylpropanal (1.08 g) was added to a mixture of exo-3-(5-chloropyrid-3-yl)-endo-3-cyano-8-azabicyclo[3.2.1]octane (2.0 g) and p-toluenesulphonic acid (0.15 g) in toluene (30 ml) and the mixture heated under Dean and Stark reflux for 3 hours. After standing at room temperature overnight the mixture was evaporated under reduced pressure to give exo-3-(5-chloropyrid-3-yl)-endo-3-cyano-8-(2-phenylprop-1-en-1-yl)-8-azabicyclo[3.2.1]octane which was used without further purification.

Sodium N-chloro-p-toluenesulphonamide (2.3 g) was added to the exo-3-(5-chloropyrid-3-yl)-endo-3-cyano-8-(2-phenylprop-1-en-1-yl)-8-azabicyclo[3.2.1]octane from the above reaction in dichloromethane (30 ml) and the mixture stirred at room temperature for 5 hours. After standing at room temperature over the weekend the mixture was stirred for 8 hours and then allowed to stand overnight. The mixture was then filtered (celite) and the residue washed with dichloromethane. The combined filtrates were washed with sodium hypochlorite (×2) and brine, dried (MgSO$_4$) and evaporated under reduced pressure. Chromatography [SiO$_2$; dichloromethane:methanol (98:2)] followed by chromatography [SiO$_2$; dichloromethane:methanol (99:1)] gave exo-3-(5-chloropyrid-3-yl)-endo-3-cyano-8-(2-phenyl-3-oxo-prop-2-yl)-8-azabicyclo[3.2.1]octane (0.43 g) m.p. 124–126° C.

EXAMPLE 32

This example illustrates the preparation of exo-3-(5-chloropyrid-3-yl)-endo-3-cyano-8-(2-phenylbut-3-en-2-yl)-8-azabicyclo[3.2.1]octane.

Sodium methoxide (0.085 g) was added in two portions to a stirred solution of methyltriphenylphosphonium bromide (0.56 g) in dimethyl sulphoxide (30 ml) at room temperature under nitrogen. The mixture was warmed to 70° C. and after 2 hours exo-3-(5-chloropyrid-3-yl)-endo-3-cyano-8-(2-phenyl-3-oxo-prop-2-yl)-8-azabicyclo[3.2.1]octane (0.30 g) in a small volume of dimethyl sulphoxide was added dropwise. After 3 hours the mixture was allowed to cool to room temperature and stand overnight. The mixture was poured into ice/water and the resulting mixture extracted with ethyl acetate (×3). The combined extracts were washed with brine (×2), dried (MgSO$_4$) and evaporated under reduced pressure. Chromatography [SiO$_2$; ethyl acetate:hexane (90:10)] gave exo-3-(5-chloropyrid-3-yl)-endo-3-cyano-8-(2-phenylbut-3-en-2-yl)-8-azabicyclo[3.2.1]octane (0.24 g).

EXAMPLE 33

This example illustrates the preparation of exo-3-(5-chloropyrid-3-yl)-endo-3-cyano-8-(2-phenyl-3-hydroxyprop-2-yl)-8-azabicyclo[3.2 1]octane.

Sodium borohydride (0.094 g) was added to a stirred solution exo-3-(5-chloropyrid-3-yl)-endo-3-cyano-8-(2-phenyl-3-oxo-prop-2-yl)-8-azabicyclo[3.2.1]octane (0.90 g) in ethanol (15 ml) under nitrogen. After 2 hours the mixture was poured into brine and the resulting mixture extracted with ethyl acetate (×2). The combined extracts were dried (MgSO$_4$), evaporated under reduced pressure and chromatographed [SiO$_2$; ethyl acetate:hexane (50:50)] to give exo-3-(5-chloropyrid-3-yl)-endo-3-cyano-8-(2-phenyl-3-hydroxyprop-2-yl)-8-azabicyclo[3.2.1]octane (0.777 g) m.p. 124–126° C.

EXAMPLE 34

This example illustrated the preparation of exo-3-(5-chloropyrid-3-yl)-endo-3-yl)-endo-3-cyano-8-(2-fluoro-2-phenylprop-1-yl)-8-azabicyclo[3.2.1]octane.

Diethylaminosulphur trifluoride (0.4 ml) and exo-3-(5-chloropyrid-3-yl)-endo-3-cyano-8-(2-phenyl-3-hydroxyprop-2-yl)-8-azabicyclo[3.2.1]octane (0.10 g) were stirred in dichloromethane (0.2 ml) at room temperature for 4 hours. The mixture was allowed to stand at room temperature over the weekend and water added. The mixture was extracted with ethyl acetate and the aqueous layer basified with saturated sodium bicarbonate solution. The aqueous layer was then extracted with ethyl acetate (×3) and the combined organic extracts were washed with sodium bicarbonate solution and brine, dried (MgSO$_4$) and evaporated under reduced pressure. chromatography [SiO$_2$; ethyl acetate:hexane (17:83)] gave exo-3-(5-chloropyrid-3-yl)-endo-3-cyano-8-(2-fluoro-2-phenylprop-1-yl)-8-azabicyclo[3.2.1]octane (0.075 g).

EXAMPLE 35

This example illustrates the preparation of exo-3-(5-chloropyrid-3-yl)-endo-3-cyano-8-(2-phenyl-3-acetoxyprop-2-yl)-8-azabicyclo[3.2.1] octane.

Triethylamine (0.06 ml) and acetyl chloride (0.029 ml) were added to a stirred solution of exo-3-(5-chloropyrid-3-yl)-endo-3-cyano-8-(2-phenyl-3-hydroxyprop-2-yl)-8-azabicyclo[3.2.1]octane (0.15 g) in dichloromethane (5 ml) at room temperature under nitrogen. After 1.5 hours dichloromethane was added and the mixture washed with water (×2) and brine, dried (MgSO$_4$) and evaporated under reduced pressure. Chromatography [SiO$_2$; ethyl acetate:hexane (20:80)] gave exo-3-(5-chloropyrid-3-yl)-endo-3- cyano-8-(2-phenyl-3-acetoxyprop-2-yl)-8-azabicyclo[3.2.1] octane (0.14 g) m.p. 130–131° C.

EXAMPLE 36

This example illustrates the preparation of exo-3-(5-chloropyrid-3-yl)-endo-3-cyano-8-formyl-8-azabicyclo [3.2.1]octane.

exo-3-(5-Chloropyrid-3-yl)-endo-3-cyano-8-azabicyclo [3.2.1]octane (3.0 g) and formic acid (1.14 ml) were heated at reflux for 4 hours. The mixture was then heated at 110° C. overnight and formic acid (1.0 ml) added. After 8 hours the mixture was allowed to cool to room temperature and stand overnight. Ethyl acetate was added and the mixture washed with 2M sodium hydroxide solution (×2), water and brine, dried (MgSO$_4$) and evaporated under reduced pressure. Chromatography [SiO$_2$; ethyl acetate:methanol (95:5)] gave exo-3-(5-chloropyrid-3-yl)-endo-3-cyano-8-formyl-8-azabicyclo[3.2.1]octane (1.675 g) m.p. 141–142° C.

EXAMPLE 37

This example illustrates the preparation of exo-3-(5-chloropyrid-3-yl)-endo-3-cyano-8-(diisopropylcarbamyl)-8-azabicyclo[3.2.1]octane.

Triethylamine (0.27 ml) followed by diisopropylcarbamyl chloride (0.317 g) was added to a stirred solution of exo-3-(5-chloropyrid-3-yl)-endo-3-cyano-8-azabicyclo[3.2.1] octane (0.40 g) in dichloromethane (5 ml) at room temperature. After 2 hours the mixture was allowed to stand at room temperature for 4 days. Dichloromethane was then added and the mixture washed with water (×2) and brine, dried (MgSO$_4$) and evaporated under reduced pressure. Filtration [SiO$_2$; ethyl acetate] gave exo-3-(5-chloropyrid-3-yl)-endo-3-cyano-8-(diisopropylcarbamyl)-8-azabicyclo[3.2.1] octane (0.12 g) m.p. 118–121° C.

EXAMPLE 38

This example illustrates the preparation of exo-3-(5-chloropyrid-3-yl)-endo-3-cyano-8-(tert-butylcarbamyl)-8-azabicyclo[3.2.1]octane.

Triethylamine (0.27 ml) followed by tert-butylisocyanate (0.22 ml) was added to a stirred solution of exo-3-(5-chloropyrid-3-yl)-endo-3-cyano-8-azabicyclo[3.2.1]octane (0.40 g) in dichloromethane (4 ml) at room temperature. After 3 hours the mixture was allowed to stand at room temperature overnight and dichloromethane then added. The mixture was then washed with water (×2) and brine, dried (MgSO$_4$) and evaporated under reduced pressure. Chromatography [SiO$_2$; diethyl ether] gave exo-3-(5-chloropyrid-3-yl)-endo-3-cyano-8-(tert-butylcarbamyl(-8-azabicyclo [3.2.1]octane (0.40 g) m.p. 62–65° C.

EXAMPLE 39

This example illustrates the preparation of (R)-exo-3-(5-chloropyrid-3-yl)-endo-3-cyano-8-(1-phenyl ethyl)-8-azabicyclo[3.2.1]octane.

Three drops of 5M hydrochloric acid were added to a mixture of 2,5-dimethoxytetrahydrofuran (16.5 g) and water (70 ml). A cooled mixture of (R)-a-methylbenzylamine (15.125 g) and 5M hydrochloric acid (30 ml) was then added followed by 1,3-acetonedicarboxylic acid (18.26 g) sodium acetate (10 g) and water (100 ml). After 5 days the mixture was basified with aqueous sodium carbonate solution and extracted with ethyl acetate. The extracts were washed with brine, dried (MgSO$_4$) and evaporated under reduced pressure. Chromatography [SiO$_2$; ethyl acetate:hexane (10:90) to (20:80)] gave (R)-8-(1-phenylethyl)-8-azabicyclo[3.2.1]octan-3-one.

Potassium t-butoxide (13.4 g) was added portionwise to a stirred mixture of gave (R)-8-(1-phenylethyl)-8-azabicyclo[3.2.1] octan-3-one (11.45 g) and tosylmethyl isocyanide (12.7 g) in dimethoxyethane (200 ml) and ethanol (6 ml) at −5° C. at such a rate to maintain the temperature below −2° C. After stirring overnight the mixture was filtered (celite) and the filtrate evaporated under reduced pressure. The residue was then dissolved in ethyl acetate, washed with water, dried (MgSO$_4$) and evaporated under reduced pressure. Chromatography [SiO$_2$; ethyl acetate:hexane (50:50)] gave (R)-exo-3-cyano-8-(1-phenylethyl)-8-azabicyclo[3.2.1]octane (3.5 g) m.p. 138–139.5° C.

Lithium bis(trimethylsilyl)amide (4.8 ml of a 1.0M solution in tetrahydrofuran) was added to a stirred solution of (R)-exo-3-cyano-8-(1-phenylethyl)-8-azabicyclo[3.2.1]octane (1.0 g) and 3,5-dichloropyridine (0.674 g) in tetrahydrofuran (20 ml) at 0° C. under nitrogen. The mixture was allowed to warm to room temperature and stand for 24 hours. Water (20 ml) was added and the mixture stirred for 30 minutes and then allowed to stand for 2 days. The mixture was extracted with ethyl acetate and the extracts washed with brine, dried (MgSO$_4$) and evaporated under reduced pressure. Chromatography [SiO$_2$; ethyl acetate:hexane (50:50)], preparative thin layer chromatography [SiO$_2$; ethyl acetate:hexane (25:75)] and recrystallisation from hexane gave (R)-exo-3-(5-chloropyrid-3-yl)-endo-3-cyano-8-(1-phenyl thyl)-8-azabicyclo[3.2.1]octane (0.46 g) m.p. 113–115° C.

EXAMPLE 40

This example illustrates the preparation of exo-3-(5-aminopyrid-3-yl)-endo-3-cyano-8-methyl-8-azabicyclo [3.2.1]octane.

Ammonia solution (35%) was added to exo-3-(5-bromopyrid-3-yl)-endo-3-cyano-8-methyl-8-azabicyclo [3.2.1]octane (0.106 g) and copper(II) sulphate hydrate (0.001 g) and the tube sealed. The mixture was heated at 100° C. for 20 hours and then 150° C. for 24 hours. The mixture was then cooled and evaporated under reduced pressure. The residue was then dissolved in methanol, charcoal added and the mixture filtered and evaporated under reduced pressure. Water and dichloromethane were added followed by ammonia solution and the resulting mixture was extracted with dichloromethane. The combined extracts were washed with brine, dried (MgSO$_4$) and evaporated under reduced pressure to give exo-3-(5-aminopyrid-3-yl)-endo-3-cyano-8-methyl-8-azabicyclo[3.2.1]octane (0.045 g) m.p. 188–190° C.

EXAMPLE 41

This example illustrates the preparation of exo-3-(5-acetylamidopyrid-3-yl)-endo-3-cyano-8-methyl-8-azabicyclo[3.2.1]octane.

Acetic anhydride (1.0 ml) was added to exo-3-(5-aminopyrid-3-yl)-endo-3-cyano-8-methyl-8-azabicyclo [3.2.1]octane (0.10 g). After 3 days dilute sodium bicarbonate solution and ethyl acetate were added followed by sodium bicarbonate and potassium carbonate to basify the mixture. The mixture was extracted with ethyl acetate and the extracts dried (MgSO$_4$) and evaporated under reduced pressure to give exo-3-(5-acetylamidopyrid-3-yl)-endo-3-cyano-8-methyl-8-azabicyclo[3.2.1]octane (0.107 g).

EXAMPLE 42

This example illustrates the preparation of exo-3-(5-chloropyrid-3-yl)-endo-3-cyano-8-(a-cyanobenzyl)-8-azabicyclo[3.2.1]octane.

exo-3-(5-Chloropyrid-3-yl)-endo-3-cyano-8-azabicyclo [3.2.1]octane (2.0 g) and benzaldehyde (0.89 ml) were added to 1M hydrochloric acid (20 ml) and the mixture stirred for 20 minutes. Sodium cyanide (0.549 g) in water (6 ml) was then added. After 18 hours ethanol (20 ml) was added to give one phase. After 6 days the reaction mixture was partitioned between ethyl acetate and water and the organic layer was washed with water and brine, dried (MgSO$_4$) and evaporated under reduced pressure. Chromatography [SiO$_2$; dichloromethane:methanol:triethylamine (99.4:0.5:0.1)] gave exo-3-(5-chloropyrid-3-yl)-endo-3-cyano-8-(a-cyanobenzyl)-8-azabicyclo[3.2.1]octane (0.104 g) m.p. 141–142° C.

EXAMPLE 43

This example illustrates the preparation of exo-3-(5-chloropyrid-3-yl)-endo-3-cyano-8-(a-carbamylbenzyl)-8-azabicyclo[3.2.1]octane.

Concentrated sulphuric acid (10 ml) was added to exo-3-(5-chloropyrid-3-yl)-endo-3-cyano-8-(a-cyanobenzyl)-8-azabicyclo[3.2.1]octane (0.51 g) and the mixture stirred for 1 hour. Ice (100 g) was added and the mixture basified with sodium bicarbonate solution. A precipitate formed which was collected by filtration, dissolved in ethyl acetate, dried (MgSO$_4$) and evaporated under reduced pressure. Chromatography [SiO$_2$; dichloromethane:methanol (99:1) to (98:2)] gave exo-3-(5-chloropyrid-3-yl)-endo-3-cyano-8-(a-carbamylbenzyl)-8-azabicyclo[3.2.1]octane (0.181 g) m.p. 193–195° C.

EXAMPLE 44

This example illustrates the preparation of exo-3-(5-iodopyrid-3-yl)-endo-3-cyano-8-methyl-8-azabicyclo[3.2.1]octane.

Nickel(II) bromide (1.55 ml of a 0.16M solution in N,N-dimethylformamide) was added to a stirred solution of tri(n-butyl)phosphine (0.124 ml) in N,N-dimethylformamide (5 ml) under nitrogen. Potassium iodide (3.96 g) was then added followed by exo-3-(5-bromopyrid-3-yl)-endo-3-cyano-8-methyl-8-azabicyclo[3.2.1]octane (1.522 g) and the mixture heated under reflux for 48 hours. The mixture was then cooled to room temperature and partitioned between water and ethyl acetate. The organic layer was dried (MgSO$_4$), evaporated under reduced pressure and chromatographed [SiO$_2$; dichloromethane:methanol (95:5)] to give exo-3-(5-iodopyrid-3-yl)-endo-3-cyano-8-methyl-8-azabicyclo[3.2.1]octane (0.399 g) m.p. 144–145° C.

EXAMPLE 45

This example illustrates the preparation of exo-3-(5-trifluoromethylpyrid-3-yl)-endo-3-cyano-8-methyl-8-azabicyclo[3.2.1]octane.

exo-3-(5-Iodopyrid-3-yl)-endo-3-cyano-8-methyl-8-azabicyclo[3.2.1]octane (0.50 g) followed by copper(I) iodide were added to a stirred solution of sodium trifluoroacetate (2.6 g) in N-methylpyrrolidinone (5 ml) and the mixture heated to 180° C. After 3 hours the mixture was cooled to room temperature, water added and extracted with dichloromethane. The organic layer was filtered and the filtrate dried (MgSO$_4$) and evaporated under reduced pressure. Diethyl ether was added and the mixture extracted repeatedly with water. The aqueous fraction was evaporated under reduced pressure, basified with potassium carbonate and extracted with diethyl ether. The extracts were washed with 1M hydrochloric acid and the aqueous fraction basified with potassium carbonate and extracted with diethyl ether. The extracts were dried (MgSO$_4$) and evaporated under reduced pressure. Preparative thin layer chromatography [Al$_2$O$_3$; diethyl ether] gave exo-3-(5-trifluoromethylpyrid-3-yl)-endo-3-cyano-8-methyl-8-azabicyclo[3.2.1]octane (0.027 g) m.p. 118.2–118.5° C.

EXAMPLE 46

This example illustrates the preparation of exo-3-(5-chloropyrid-3-yl)-endo-3-cyano-8-(mercaptothiocarbonyl)-8-azabicyclo[3.2.1]octane.

Carbon disulphide (0.12 ml) was added to a stirred solution of exo-3-(5-chloropyrid-3-yl)-endo-3-cyano-8-azabicyclo[3.2.1]octane (0.50 g) in ethanol (5 ml) at room temperature under nitrogen. After 4 hours the mixture was allowed to stand overnight. The precipitate was collected by filtration and washed with hexane to give exo-3-(5-chloropyrid-3-yl)-endo-3-cyano-8-(mercaptothiocarbonyl)-8-azabicyclo[3.2.1]octane (0.509 g) m.p. 224° C. (decomposed).

EXAMPLE 47

This example illustrates the preparation of exo-3-(5-chloropyrid-3-yl)-endo-3-cyano-8-(fluorocarbonyl)-8-azabicyclo[3.2.1]octane.

Iodomethane (0.08 ml) was added to a stirred mixture of exo-3-(5-chloropyrid-3-yl)-endo-3-cyano-8-(mercaptothiocarbonyl)-8-azabicyclo[3.2.1]octane (0.40 g) in dimethyl sulphoxide (3 ml) at room temperature. After 3 hours water was added and the mixture extracted with dichloromethane (×3). The combined extracts were washed with water (×2) and brine, dried (MgSO$_4$) and evaporated under reduced pressure. Dichloromethane was added and the mixture washed with brine (×2), dried (MgSO$_4$) and evaporated under reduced pressure to give exo-3-(5-chloropyrid-3-yl)-endo-3-cyano-8-(methylmercaptothiocarbonyl)-8-azabicyclo[3.2.1]octane (0.187 g).

Tetra(n-butyl)ammonium dihydrogentrifluoride (0.48 g) was added to a solution of exo-3-(5-chloropyrid-3-yl)-endo-3-cyano-8-(methylmercaptothiocarbonyl)-8-azabicyclo [3.2.1]octane (0.180 g) in dichloromethane at 0° C. under nitrogen. N-Bromosuccinimide (0.38 g) was then added. After 10 minutes the mixture was warmed to room temperature. After 2 hours the mixture was cooled to 0° C. and allowed to stand over the weekend. The mixture was then stirred at room temperature for 8 hours and allowed to stand overnight. The mixture was diluted with dichloromethane and sodium bicarbonate and sodium bisulphite solutions added. The mixture was extracted with dichloromethane and the extracts dried (MgSO$_4$) and evaporated under reduced pressure. Ethyl acetate was added and the mixture washed with water (×2) and brine, dried (MgSO$_4$) and evaporated under reduced pressure. Chromatography [SiO$_2$; diethyl ether:hexane (80:20)] gave exo-3-(5-chloropyrid-3-yl)-endo-3-cyano-8-(fluorocarbonyl)-8-azabicyclo[3.2.1]octane (0.10 g) m.p. 165–167° C.

EXAMPLE 48

This example illustrates the preparation of exo-3-(5-chloropyrid-3-yl)-endo-3-cyano-8-(2,2-difluoroethyl)-8-azabicyclo[3.2.1]octane.

2,2-Difluoroethyl bromide (1.08 g), potassium carbonate (1.38 g), potassium iodide (0.30 g) and exo-3-(5-chloropyrid-3-yl)-endo-3-cyano-8-azabicyclo[3.2.1]octane (1.238 g) were stirred at 50° C. in ethanol (10 ml). After 8 hours the mixture was allowed to stand at room temperature for 3 days. 2,2-Difluoroethyl bromide (1.08 g), was then added and the mixture heated under reflux for 48 hours. 2.2-Difluoroethyl bromide (1.08 g) and potassium carbonate (1.38 g) were then added and the mixture heated under reflux for 24 hours. 2,2-Difluoroethyl bromide (1.08 g) was then added and the mixture heated under reflux for 24 hours. The mixture was then cooled to room temperature and water added. The mixture was extracted with dichloromethane (×2) and the combined extracts washed with brine, dried (MgSO$_4$) and evaporated under reduced pressure. Chromatography [SiO$_2$; dichloromethane:methanol (96:4)] gave exo-3-(5-chloropyrid-3-yl)-endo-3-cyano-8-(2,2-difluoroethyl)-8-azabicyclo[3.2.1]octane (0.278 g) m.p. 101–104° C.

EXAMPLE 49

This example illustrates the preparation of exo-3-(5-chloropyrid-3-yl)-endo-3-cyano-8-(2-phenylethyl)-8-azabicyclo[3.2.1]octane.

2-Phenylethyl bromide (0.222 g), potassium carbonate (0.345 g) and exo-3-(5-chloropyrid-3-yl)-endo-3-cyano-8-azabicyclo[3.2.1]octane (0.248 g) were heated under reflux in ethanol (2 ml) for 9 hours. 2-Phenylethyl bromide (0.1 g) was added and the mixture refluxed for 5 hours. The mixture was then cooled to room temperature and water added. The mixture was extracted with dichloromethane (×2) and the combined extracts washed with brine, dried (MgSO$_4$) and evaporated under reduced pressure. Chromatography [SiO$_2$; dichloromethane:methanol (98:2)] gave exo-3-(5-chloropyrid-3-yl)-endo-3-cyano-8-(2-phenylethyl)-8-azabicyclo[3.2.1]octane (0.08 g).

EXAMPLE 50

This example illustrates the preparation of exo-3-(5-hydroxypyrid-3-yl)-endo-3-cyano-8-methyl-8-azabicyclo[3.2.1]octane.

Pyridinium hydrochloride (1.0 g) and exo-3-(5-methoxypyrid-3-yl)-endo-3-cyano-8-cyano-8-methyl-8-azabicyclo[3.2.1]octane (0.20 g) were heated together at 150° C. for 5 hours. The mixture was then cooled to room temperature, water added and the mixture basified with sodium bicarbonate solution and extracted with ethyl acetate (×3). The aqueous fraction was neutralised with dilute hydrochloric acid and extracted with ethyl acetate (×3). The combined organic extracts were washed with water, dried (MgSO$_4$) and evaporated under reduced pressure. Chromatography [SiO$_2$; dichloromethane:methanol (90:10) to (80:20)] gave a gum which crystallised on addition of diethyl ether to give exo-3-(5-hydroxypyrid-3-yl)-endo-3-cyano-8-methyl-8-azabicyclo[3.2.1]octane (0.049 g) m.p. 171–172° C.

EXAMPLE 51

This example illustrates the preparation of exo-3-(5-chloropyrid-3-yl)-endo-3-cyano-8-benzyl-8-azabicyclo[3.2.1]octane.

exo-3-Cyano-8-methyl-8-azabicyclo[3.2.1]octane (0.5 g) in tetrahydrofuran (3 ml) was added to a solution of lithium diisopropylamide [made by adding n-BuLi (1.6 ml of a 2.5 M solution in hexane) to diisopropylamine (0.4 g) in tetrahydrofuran (3 ml)] at −25° C. under nitrogen. After 15 minutes at the mixture was cooled to −78° C. and 3,5-dichloropyridine (0.588 g) in tetrahydrofuran (3 ml) was added. After 1 hour the mixture was allowed to warm to room temperature and stand overnight. Water was then added and the resulting mixture extracted with ethyl acetate (×3). The combined extracts were washed with brine and water, dried (MgSO$_4$) and evaporated under reduced pressure. Chromatography [SiO$_2$; dichloromethane:methanol (90:10)] gave exo-3-(5-chloropyrid-3-yl)-endo-3-cyano-8-methyl-8-azabicyclo[3.2.1]octane (0.249 g).

Vinyl chloroformate (2.6 ml) in tetrahydrofuran (5 ml) was added to a stirred solution of exo-3-(5-chloropyrid-3-yl)-endo-3-cyano-8-methyl-8-azabicyclo[3.2.1]octane (2.6 g) in tetrahydrofuran (25 ml) at 0° C. The mixture was allowed to warm to room temperature over 1 hour, refluxed for 2 hours and then allowed to cool to room temperature. After 20 hours the mixture was partitioned between water and ethyl acetate and the organic layer was separated, washed with water and dried (MgSO$_4$). Evaporation under reduced pressure gave exo-3-(5-chloropyrid-3-yl)-endo-3-cyano-8-(vinyloxycarbonyl)-8-azabicyclo[3.2.1]octane (2.0 g).

exo-3-(5-Chloropyrid-3-yl)-endo-3-cyano-8-(vinyloxycarbonyl)-8-azabicyclo[3.2.1]octane (2.6 g) was dissolved in methanol (50 ml) and concentrated hydrochloric acid (7 ml) added. The mixture was refluxed for 3 hours after which the mixture was evaporated under reduced pressure and basified with aqueous sodium carbonate. The resulting mixture was extracted with ethyl acetate and evaporated under reduced pressure to give a brown solid. This was then washed with hexane to give exo-3-(5-chloropyrid-3-yl)-endo-3-cyano-8-azabicyclo[3.2.1]octane (1.2 g).

exo-3-(5-Chloropyrid-3-yl)-endo-3-cyano-8-azabicyclo[3.2.1]octane (0.104 g) in ethanol (5 ml) was added to benzyl bromide (0.079 g) and potassium carbonate (0.12 g) and the mixture refluxed for 18 hours. After cooling to room temperature the mixture was evaporated under reduced pressure and partitioned between water and ethyl acetate. The organic layer was separated and evaporated under reduced pressure. Preparative thin layer chromatography [SiO$_2$; dichloromethane:methanol (97:3)] gave exo-3-(5-chloropyrid-3-yl)-endo-3-cyano-8-benzyl-8-azabicyclo[3.2.1]octane (0.077 g).

EXAMPLE 52

This example illustrates the preparation of exo-3-(5-chloropyrid-3-yl)-endo-3-cyano-8-(pentafluorophenylmethyl)-8-azabicyclo[3.2.1]octane.

exo-3-(5-Chloropyrid-3-yl)-endo-3-cyano-8-azabicyclo[3.2.1]octane (0.248 g), 2,3,4,5,6-pentafluorobenzyl bromide (0.313 g), potassium carbonate (0.345 g) and ethanol (2 ml) were stirred under reflux for 3 hours. The mixture was then evaporated under reduced pressure and water added. The mixture was then extracted with dichloromethane (×3) and the combined extracts were washed with brine, dried (MgSO$_4$) and evaporated under reduced pressure to give an oil which crystallised on standing. The crystals were washed with a small volume of ether to give exo-3-(5-chloropyrid-3-yl)-endo-3-cyano-8-(pentafluorophenylmethyl)-8-azabicyclo[3.2.1]octane (0.258 g) m.p. 143–144° C.

EXAMPLE 53

This example illustrates the preparation of potassium exo-3-(5-chloropyrid-3-yl)-endo-3-cyano-8-(4-carboxylatobenzyl)-8-azabicyclo[3.2.1]octane.

exo-3-(5-Chloropyrid-3-yl)-endo-cyano-8-azabicyclo[3.2.1]octane (0.248 g) 4-bromomethylbenzoic acid (0.258 g), potassium carbonate (0.345 g) and ethanol (2 ml) were stirred under reflux for 2.5 hours. The mixture was then diluted with ethanol, filtered and the filtrate evaporated under reduced pressure to give potassium exo-3-(5-chloropyrid-3-yl)-endo-3-cyano-8-(4-carboxylatobenzyl)-8-azabicyclo[3.2.1]octane (0.292 g).

EXAMPLE 54

This example illustrates the preparation of exo-3-(5-chloropyrid-3-yl)-endo-3-cyano-8-(3-chloro-4-fluorobenzyl)-8-azabicyclo[3.2.1]octane.

exo-3-(5-Chloropyrid-3-yl)-endo-3-cyano-8-azabicyclo[3.2.1]octane (0.495 g), 3-chloro-4-fluorobenzaldehyde (0.317 g) and formic acid (96%, 0.230 g) were heated under reflux for 5 hours. The mixture was then cooled to room temperature, basified with dilute sodium hydroxide and extracted with dichloromethane (×2). The combined extracts were washed with brine, dried ($MgSO_4$), and evaporated under reduced pressure. Chromatography [$SiO_2$; dichloromethane:methanol (100:0) to (95:5)] gave exo-3-(5-chloropyrid-3-yl)-endo-3-cyano-8-(3-chloro-4-fluorobenzyl)-8-azabicyclo[3.2.1]octane (0.290 g) m.p. 95–97° C.

EXAMPLE 55

This example illustrates the preparation of exo-3-(5-chloropyrid-3-yl)-endo-3-cyano-8-(pyrid-2-ylmethyl)-8-azabicyclo[3.2.1]octane.

2-Picolyl chloride hydrochloride (0.361 g), potassium carbonate (0.828 g) and exo-3-(5-chloropyrid-3-yl)-endo-3-cyano-8-azabicyclo[3.2.1]octane (0.495 g) were heated under reflux in ethanol (4 ml) for 2 hours. The mixture was then cooled to room temperature and water added. The mixture was extracted with dichloromethane (×2) and the combined extracts washed with brine, dried ($MgSO_4$) and evaporated under reduced pressure. Chromatography [$SiO_2$; dichloromethane:methanol (100:0) to (95:5)] gave exo-3-(5-chloropyrid-3-yl)-endo-3-cyano-8-(pyrid-2-ylmethyl)-8-azabicyclo[3.2.1]octane (0.447 g) m.p. 123–125° C.

EXAMPLE 56

This example illustrates the preparation of exo-3-(5-chloropyrid-3-yl)-endo-3-cyano-8-((2-methylthiazol-4-yl)methyl)-8-azabicyclo[3.2.1]octane.

4-Chloromethyl-2-methylthiazole hydrochloride (0.202 g), potassium carbonate (0.483 g) and exo-3-(5-chloropyrid-3-yl)-endo-3-cyano-8-azabicyclo[3.2.1]octane (0.247 g) were heated under reflux in ethanol (2 ml) for 1.5 hours. 4-Chloromethyl-2-methylthiazole hydrochloride (0.40 g) was then added and the mixture refluxed for 30 minutes. The mixture was then cooled to room temperature and water added. The mixture was extracted with dichloromethane (×2) and the combined extracts washed with brine, dried ($MgSO_4$) and evaporated under reduced pressure. Chromatography [$SiO_2$; dichloromethane:methanol (99:1) to (95:5)] gave exo-3-(5-chloropyrid-3-yl)-endo-3-cyano-8-((2-methylthiazol-4-yl)methyl)-8-azabicyclo[3.2.1]octane (0.269 g) m.p. 81–83° C.

EXAMPLE 57

This example illustrates the preparation of exo-3-(5-chloropyrid-3-yl)-endo-3-cyano-8-((3,5-dimethylisoxazol-4-yl)methyl-8-azabicyclo[3.2.1]octane.

4-Chloromethyl-3,5-dimethylisoxazole (0.160 g), potassium carbonate (0.345 g), potassium iodide (0.02 g) and exo-3-(5-chloropyrid-3-yl)-endo-3-cyano-8-azabicyclo[3.2.1]octane (0.247 g) were heated under reflux in ethanol (2 ml) for 3 hours. The mixture was then cooled to room temperature and water added. The mixture was extracted with dichloromethane (×2) and the combined extracts washed with brine, dried ($MgSO_4$) and evaporated under reduced pressure. Filtration [$SiO_2$; dichloromethane:methanol (98:2)] gave exo-3-(5-chloropyrid-3-yl)-endo-3-cyano-8-((3,5-dimethylisoxazol-4-yl)methyl)-8-azabicyclo[3.2.1]octane (0.258 g) m.p. 95–99° C.

EXAMPLE 58

This example illustrates the preparation of exo-3-(5-chloropyrid-3-yl)-endo-3-cyano-8-(5-chlorothiophen-2-yl)-8-azabicyclo[3.2.1]octane.

2-Chloro-5-chloromethylthiophene (0.367 g), potassium carbonate (0.690 g) and exo-3-(5-chloropyrid-3-yl)-endo-3-cyano-8-azabicyclo[3.2.1]octane (0.495 g) were heated under reflux in ethanol (2 ml) for 1.5 hours. Potassium iodide (0.02 g) was then added and the mixture refluxed for 1.5 hours. The mixture was then cooled to room temperature and water added. The mixture was extracted with dichloromethane (×2) and the combined extracts washed with brine, dried ($MgSO_4$) and evaporated under reduced pressure. Chromatography [$SiO_2$; dichloromethane:methanol (100:0) to (96:4)] gave exo-3-(5-chloropyrid-3-yl)-endo-3-cyano-8-(5-chlorothiophen-2-yl)-8-azabicyclo[3.2.1]octane (0.37 g) m.p. 119–121° C.

EXAMPLE 59

This example illustrates the preparation of exo-3-(5-chloropyrid-3-yl)-endo-3-cyano-8-((5-chloro-1,2,3-thiadiazol-4-yl)methyl)-8-azabicyclo[3.2.1]octane.

5-Chloro-4-chloromethyl-1,2,3-thiadiazole (0.187 g), potassium carbonate (0.345 g) and exo-3-(5-chloropyrid-3-yl)-endo-3-cyano-8-azabicyclo[3.2.1]octane (0.248 g) were heated under reflux in ethanol (2 ml) for 4 hours. The mixture was then cooled to room temperature and water added. The mixture was extracted with dichloromethane (×2) and the combined extracts washed with brine, dried ($MgSO_4$) and evaporated under reduced pressure. Chromatography [$SiO_2$; dichloromethane:methanol (100:0) to (98:2)] gave exo-3-(5-chloropyrid-3-yl)-endo-3-cyano-8-((5-chloro-1,2,3-thiadiazol-4-yl)methyl)-8-azabicyclo[3.2.1]octane (0.148 g).

EXAMPLE 60

This example illustrates the preparation of exo-3-(5-fluoropyrid-3-yl)-endo-3-cyano-8-methyl-8-azabicyclo[3.2.1]octane.

exo-3-(5-Aminopyrid-3-yl)-endo-3-cyano-8-methyl-8-azabicyclo[3.2.1]octane (0.40 g) in dichloromethane (150 ml) was added to boron trifluoride etherate (1.5 ml) at −10 to −15° C. After a few minutes t-butyl nitrite (2 ml) was added and the mixture allowed to warm to room temperature and stand overnight. The solid precipitate was collected and heated to cause decomposition. The residue was dissolved in 2M hydrochloric acid, washed with ethyl acetate, basified and extracted with ethyl acetate. The extracts were dried ($MgSO_4$), evaporated under reduced pressure and chromatographed [$SiO_2$; dichloromethane:methanol (90:10)] to give exo-3-(5-fluoropyrid-3-yl)-endo-3-cyano-8-methyl-8-azabicyclo[3.2.1]octane (0.089 g).

EXAMPLE 61

This example illustrates the preparation of exo-3-(5-(pyrrol-1-yl)pyrid-3-yl)-endo-3-cyano-8-methyl-8-azabicyclo[3.2.1]octane.

2,5-Dimethoxytetrahydrofuran (0.53 ml) was added to a mixture of exo-3-(5-aminopyrid-3-yl)-endo-3-cyano-8-methyl-8-azabicyclo[3.2.1]octane and acetic acid (13 ml). After 5 minutes the mixture was heated at reflux for 1 hour and then allowed to cool to room temperature and stand overnight. Ethyl acetate was added and the mixture extracted with 2M hydrochloric acid and water. The combined extracts were basified with potassium carbonate and extracted with ethyl acetate. The extracts were dried (MgSO$_4$) and evaporated under reduced pressure to give exo-3-(5-(pyrrol-1-yl)pyrid-3-yl)-endo-3-cyano-8-methyl-8-azabicyclo[3.2.1]octane (0.105 g).

EXAMPLE 62

This example illustrates the preparation of exo-3-(5-(1-ethoxyvinyl)pyrid-3-yl)-endo-3-cyano-8-methyl-8-azabicyclo[3.2.1]octane.

(1-Ethoxyvinyl)tri-n-butyltin ((0.82 ml) was added to a stirred mixture of exo-3-(5-iodopyrid-2-yl)-endo-3-cyano-8-methyl-8-azabicyclo[3.2.1]octane (0.817 g) and N,N-dimethylformamide (30 ml) at room temperature under nitrogen. Bis(triphenylphosphine)palladium(II) chloride (0.65 g) was then added and the mixture heated at 130° C. for 3 hours. The mixture was then allowed to cool to room temperature, water added and the mixture extracted with dichloromethane (×3). The combined extracts were washed with brine, dried (MgSO$_4$) and evaporated under reduced pressure. Chromatography [SiO$_2$; dichloromethane:methanol (91:9)] followed by chromatography [SiO$_2$; dichloromethane:methanol (98:2) to (92:8] gave exo-3-(5-(1-ethoxyvinyl)pyrid-3-yl)-endo-3-cyano-8-methyl-8-azabicyclo[3.2.1]octane (0.22 g).

EXAMPLE 63

This example illustrates the preparation of exo-3-(5-acetylpyrid-3-yl)-endo-3-cyano-8-methyl-8-azabicyclo[3.2.1]octane.

2M Hydrochloric acid (1 ml) was added to a stirred mixture of exo-3-(5-(1-ethoxyvinyl)pyrid-3-yl)-endo-3-cyano-8-methyl-8-azabicyclo[3.2.1]octane (0.18 g) in acetone (2 ml). After 3 hours the mixture was allowed to stand overnight. The mixture was poured onto saturated sodium bicarbonate solution and the resulting mixture extracted with dichloromethane (×3). The combined extracts were dried (MgSO$_4$), evaporated under reduced pressure and chromatographed [SiO$_2$; dichloromethane:methanol (93:7)] to give exo-3-(5-acetylpyrid-3-yl)-endo-3-cyano-8-methyl-8-azabicyclo[3.2.1]octane (0.13 g).

EXAMPLE 64

This example illustrates the preparation of exo-3-(5-ethynylpyrid-3-yl)-endo-3-cyano-8-methyl-8-azabicyclo[3.2.1]octane.

exo-3-(5-Iodopyrid-3-yl)-endo-3-cyano-8-methyl-8-azabicyclo[3.2.1]octane (0.50 g) in tetrahydrofuran (1 ml) was added dropwise to a stirred mixture of trimethylsilylacetylene (0.22 ml), diethylamine (1.13 ml), copper(I) iodide (0.01 g) and tetrakis(triphenylphosphine)palladium (0) (0.02 g) at room temperature under nitrogen. After 3 hours the mixture was allowed to stand at room temperature for 24 hours and then evaporated under reduced pressure. Dichloromethane (10 ml) was added followed by tetrabutylammonium fluoride (1.7 ml of a 1M solution in tetrahydrofuran) and the mixture stirred at room temperature for 1.5 hours. Water was added and the mixture extracted with dichloromethane (×2). The combined extracts were washed with brine, dried (MgSO$_4$), evaporated under reduced pressure and chromatographed [SiO$_2$; dichloromethane:methanol (95:5) to (90:10)] to give a crude product. Chromatography [SiO$_2$; dichloromethane:methanol (92:8)] followed by dissolving the product in dichloromethane, washing with water (×2) and brine, drying (MgSO$_4$) and evaporating under reduced pressure gave exo-3-(5-ethynylpyrid-3-yl)-endo-3-cyano-8-methyl-8-azabicyclo[3.2.1]octane (0.40 g).

EXAMPLE 65

This example illustrates the preparation of exo-3-(5-chloropyrid-3-yl)-endo-3-cyano-8-(1-hydroxy-1-cyano-2-phenylprop-2-yl)-8-azabicyclo[3.2.1]octane.

Sodium cyanoborohydride (0.033 g) was added to a stirred solution of isopropylamine (0.045 ml) and exo-3-(5-chloropyrid-3-yl)-endo-3-cyano-8-(2-phenyl-3-oxo-prop-2-yl)-8-azabicyclo[3.2.1]octane (0.20 g) in methanol (2 ml). Methanolic hydrogen chloride was then added to give pH5. After 2 hours the mixture was allowed to stand at room temperature for 2 days and isopropylamine (0.045 ml) and sodium cyanoborohydride (0.033 g) were added. After stirring at room temperature for 6 hours saturated sodium bicarbonate was added and the mixture extracted with dichloromethane (×3). The combined extracts were washed with brine, dried (MgSO$_4$), evaporated under reduced pressure and chromatographed [SiO$_2$; dichloromethane:methanol (100:0) to (90:10)] to give exo-3-(5-chloropyrid-3-yl)-endo-3-cyano-8-(1-hydroxy-1-cyano-2-phenylprop-2-yl)-8-azabicyclo[3.2.1]octane (0.75 g) m.p. 172–175° C.

EXAMPLE 66

This example illustrates the preparation of exo-3-(5-chloropyrid-3-yl)-endo-3-cyano-8-(2-(isopropylamino)-2-phenylprop-1-yl)-8-azabicyclo[3.2.1]octane.

Triethylamine (0.1 ml) and methanesulphonyl chloride (0.053 ml) were added to a stirred solution of exo-3-(5-chloropyrid-3-yl)-endo-3-cyano-8-(2-phenyl-3-hydroxyprop-2-yl)-8-azabicyclo[3.2.1]octane (0.25 g) in dichloromethane (5 ml) at room temperature. After 2 hours isopropylamine (0.65 ml) was added. After 2 hours the mixture was allowed to stand at room temperature overnight and dichloromethane then added. The mixture was washed with water (x2) and brine, dried (MgSO$_4$), evaporated under reduced pressure and chromatographed [SiO$_2$; dichloromethane:methanol (98:2) to (95:5)] to give exo-3-(5-chloropyrid-3-yl)-endo-3-cyano-8-(2-(isopropylamino)-2-phenylprop-1-yl)-8-azabicyclo[3.2.1]octane (0.24 g).

EXAMPLE 67

This example illustrates the preparation of exo-3-(5-chloropyrid-3-yl)-endo-3-cyano-8-cyanomethyl-8-azabicyclo[3.2.1]octane.

Bromoacetonitrile (0.85 ml) was added to a mixture of exo-3-(5-chloropyrid-3-yl)-endo-3-cyano-8-azabicyclo[3.2.1]octane (2.0 g) and potassium carbonate (2.23 g) in ethanol (10 ml) and the mixture heated at reflux for 3 hours. The mixture was then cooled to room temperature, filtered (celite) and washed through with dichloromethane. The filtrates were evaporated under reduced pressure, chromatographed [SiO$_2$; dichloromethane:methanol (99:1)] and recrystallised (ethyl acetate/hexane) to give exo-3-(5-chloropyrid-3-yl)-endo-3-cyano-8-cyanomethyl-8-azabicyclo[3.2.1]octane (1.36 g), m.p. 149–151° C.

EXAMPLE 68

This example illustrates the preparation of exo-3-(5-chloropyrid-3-yl)-endo-3-cyano-8-(1-ethoxycarbonyl) ethyl)-8-azabicyclo[3.2.1]octane.

Ethyl 2-bromopropionate (0.29 ml) was added to a mixture of exo-3-(5-chloropyrid-3-yl)-endo-3-cyano-8-azabicyclo[3.2.1]octane (0.5 g) and potassium carbonate (0.42 g) in tetrahydrofuran (8 ml) and the mixture heated at reflux for 24 hours. The mixture was then cooled to room temperature, filtered (celite) and washed through with dichloromethane. The filtrates were evaporated under reduced pressure and chromatographed [SiO$_2$; dichloromethane:methanol (100.0 to (98:2)] to give exo-3-(5-chloropyrid-3-yl)-endo-3-cyano-8-(1-(ethoxycarbonyl) ethyl)-8-azabicyclo[3.2.1]octane (0.49 g).

EXAMPLE 69

This example illustrates the preparation of exo-3-(5-chloropyrid-3-yl)-endo-3-cyano-8-(6-fluoropyrid-2-yl)-8-azabicyclo[3.2.1]octane.

2,6-Difluoropyridine (0.37 ml) potassium carbonate (1.12 g) and exo-3-(5-chloropyrid-3-yl)-endo-3-cyano-8-azabicyclo[3.2.1]octane (1.0 g) were heated at 140° C. in N-methylpyrrolidinone (10 ml) for a total of 8 hours. The mixture was then cooled to room temperature, poured into water and the resulting mixture extracted with ethyl acetate (x3). The combined extracts were washed with brine, dried (MgSO$_4$), evaporated under reduced pressure and chromatographed [SiO$_2$; hexane:ethyl acetate (90:10)] to give exo-3-(5-chloropyrid-3-yl)-endo-3-cyano-8-(6-fluoropyrid-2-yl)-8-azabicyclo[3.2.1]octane (0.796 g) m.p. 131.5–132.5° C.

EXAMPLE 70

This example illustrates the preparation of exo-3-(5-chloropyrid-3-yl)-endo-3-cyano-8-(5-chlorothiazol-2-yl)-8-azabicyclo[3.2.1]octane.

2-Bromo-5-chlorothiazole (2.4 g), potassium carbonate (1.67 g) and exo-3-(5-chloropyrid-3-yl)-endo-3-cyano-8-azabicyclo[3.2.1]octane (1.0 g) were heated at 140° C. in N-methylpyrrolidinone (10 ml) for a total of 10 hours. The mixture was then cooled to room temperature, poured into water and the resulting mixture extracted with ethyl acetate (x3). The combined extracts were washed with brine, dried (MgSO$_4$), evaporated under reduced pressure and chromatographed [SiO$_2$; hexane;ethyl acetate (90:10)]. Recrystallisation (hexane) gave exo-3-(5-chloropyrid-3-yl)-endo-3-cyano-8-(5-chlorothiazol-2-yl)-8-azabicyclo[3.2.1]octane (0.17 g) m.p. 111–112° C.

EXAMPLE 71

This example illustrates the preparation of exo-3-(5-chloropyrid-3-yl)-endo-3-cyano-8-pentafluorophenyl-8-azabicyclo[3.2.1]octane.

Hexafluorobenzene (0.93 ml), potassium carbonate (1.12 g) and exo-3-(5-chloropyrid-3-yl)-endo-3-cyano-8-azabicyclo[3.2.1]octane (1.0 g) were heated at 150° C. in N-methylpyrrolidinone (10 ml) for 5 hours. Hexafluorobenzene (0.93 ml) and potassium carbonate (1.12 g) were added and the mixture heated at 160° C. for 7 hours. The mixture was then cooled to room temperature, poured into water and the resulting mixture extracted with ethyl acetate (x3). The combined extracts were washed with brine, dried (MgSO$_4$), evaporated under reduced pressure and chromatographed [SiO$_2$; hexane:ethyl acetate (90:10)] to give exo-3-(5-chloropyrid-3-yl)-endo-3-cyano-8-pentafluorophenyl-8-azabicyclo[3.2.1]octane (0.55 g).

EXAMPLE 72

This example illustrates the preparation of exo-3-(5-chloropyrid-3-yl)-endo-3-cyano-8-cyano-8-azabicyclo [3.2.1]octane.

Tosyl cyanide (0.88 ml) was added dropwise to a stirred mixture of exo-3-(5-chloropyrid-3-yl)-endo-3-cyano-8-azabicyclo[3.2.1]octane (1.0 g) and N,N-diisopropylethylamine (0.85 ml) in tetrahydrofuran (5 ml) at room temperature. After 6 hours the mixture was allowed to stand at room temperature overnight, poured into water and extracted with ethyl acetate (x3). The combined extracts were washed with water and brine, dried (MgSO$_4$), evaporated under reduced pressure and chromatographed [SiO$_2$; hexane:ethyl acetate (90:10)]. Recrystallisation (hexane/ethyl acetate) gave exo-3-(5-chloropyrid-3-yl)-endo-3-cyano-8-cyano-8-azabicyclo[3.2.1]octane (0.20 g) m.p. 168–170° C.

EXAMPLE 73

This example illustrates the preparation of exo-3-(5-chloropyrid-3-yl)-endo-3-cyano-8-methoxy-8-azabicyclo [3.2.1]octane.

N,N-Diisoproylethylamine (14.5 ml) was added dropwise to a stirred suspension of O-methylhydroxylamine hydrochloride (2.32 g) in isopropyl alcohol (25 ml). After 30 minutes cyclohepta-2,6-dienone (3.0 g) in isopropyl alcohol (5 ml) was added dropwise. After 24 hours N,N-diisopropylethylamine (4.9 ml) was added. After 6 hours the mixture was allowed to stand at room temperature overnight. The mixture was evaporated under reduced pressure, diethyl ether added and the resulting mixture extracted with 2M hydrochloric acid (x3). The combined aqueous fractions were washed with diethyl ether (x3), neutralised with sodium hydroxide and extracted with diethyl ether (x3). The combined extracts were washed with brine, dried (MgSO$_4$) and evaporated under reduced pressure. Kugelrohr distillation gave 8-methoxy-8-azabicyclo[3.2.1]octan-3-one (0.86 g).

Tosylmethyl isocyanide (2.52 g) was added to a stirred suspension of potassium t-butoxide (2.17 g) in 1,2-dimethoxyethane (10 ml) at such a rate to keep the temperature below 10° C. After 45 minutes 8-methoxy-8-azabicyclo[3.2.1]octan-3-one (1.0 g) in 1,2-dimethoxyethane (10 ml) was added dropwise. After 30 minutes the mixture was allowed to warm to room temperature. After 4 hours the mixture was allowed to stand at room temperature overnight and water was then added. The resulting mixture was extracted with ethyl acetate (x3) and the combined extracts washed with brine, dried (MgSO$_4$)and evaporated under reduced pressure. Chromatography [SiO$_2$; hexane:ethyl acetate (90:10)] gave exo-3-cyano-8-methoxy-8-azabicyclo[3.2.1]octane (0.40 g).

Lithium bis(trimethylsilyl)amide (2.42 ml of a 1M solution in tetrahydrofuran) was added dropwise to a stirred solution of exo-3-cyano-8-methoxy-8-azabicyclo[3.2.1] octane (0.40 g) and 3,5-dichloropyridine (0.358 g) in tetrahydrofuran (5 ml) at 0° C. After 1 hour the mixture was allowed to warm to room temperature. After 5 hours water was added and the mixture extracted with ethyl acetate (x3). The combined extracts were washed with brine, dried (MgSO$_4$) and evaporated under reduced pressure. Preparative thin layer chromatography [SiO$_2$; ethyl acetate] gave exo-3-(5-chloropyrid-3-yl)-endo-3-cyano-8-methoxy-8-azabicyclo[3.2.1]octane (0.192 g) m.p. 1075.–108.5° C.

EXAMPLE 74

This example illustrates the preparation of exo-3-(5-chloropyrid-3-yl)-endo-3-cyano-8-(2-(ethoxycarbonyl) ethyl)-8-azabicyclo[3.2.1]octane.

Sodium hydride (0.095 g of an 80% dispersion in oil) was added to exo-3-(5-chloropyrid-3-yl)-endo-3-cyano-8-azabicyclo[3.2.1]octane (0.75 g) and ethyl acrylate (2.0 g) in tetrahydrofuran. The mixture was refluxed for 8 hours then allowed to cool to room temperature, water added and the mixture extracted with ethyl acetate (x2). The combined extracts were washed with brine, dried ($MgSO_4$) and evaporated under reduced pressure. Chromatography [$SiO_2$; chloroform/methanol (95:5)] followed by chromatography [$SiO_2$; ethyl acetate:dichloromethane (80:20)] gave exo-3-(5-chloropyrid-3-yl)-endo-3-cyano-8-(2-(ethoxycarbonyl)ethyl)-8-azabicyclo[3.2.1]octane.

EXAMPLE 75

This example illustrates the preparation of exo-3-(5-chloropyrid-3-yl)-endo-3-cyano-8-(2-carboxyethyl)-8-azabicyclo[3.2.1]octane.

3M Sodium hydroxide (4 ml) was added to a stirred solution of exo-3-(5-chloropyrid-3-yl)-endo-3-cyano-8-(2-(ethoxycarbonyl)ethyl)-8-azabicyclo[3.2.1]octane (0.41 g) in ethanol (8 ml) at room temperature. After 24 hours the mixture was basified to pH9 and evaporated under reduced pressure. The product was azeotroped with methanol/toluene and chromatographed [$SiO_2$; dichloromethane:methanol (75:25)] to give exo-3-(5-chloropyrid-3-yl)-endo-3-cyano-8-(2-carboxyethyl)-8-azabicyclo[3.2.1]octane (0.21 g) m.p. 180–181° C.

EXAMPLE 76

This example illustrates the preparation of exo-3-(5-chloropyrid-3-yl)-endo-3-cyano-8-(O,O-diethylphosphonomethyl)-8-azabicyclo[3.2.1]octane.

exo-3-(5-chloropyrid-3-yl)-endo-3-cyano-8-azabicyclo[3.2.1]octane (0.20 g), O,O-diethylphosphonomethyl triflate (0.245 g) and potassium carbonate (0.15 g) were heated under reflux in tetrahydrofuran (8 ml). After 3 hours the mixture was cooled to room temperature, filtered and evaporated under reduced pressure. Chromatography [$SiO_2$; dichloromethane:methanol (96:4)] followed by high pressure liquid chromatography [$SiO_2$; dichloromethane:methanol (96:4)] gave exo-3-(5-chloropyrid-3-yl)-endo-3-cyano-8-(O,O-diethylphosphonomethyl)-8-azabicyclo[3.2.1]octane m.p. 69–70° C.

EXAMPLE 77

This example illustrates the preparation of exo-3-(5-chloropyrid-3-yl)-endo-3-cyano-8-phosphonomethyl-8-azabicyclo[3.2.1]octane.

Trimethylsilyl bromide (1.5 ml) was added dropwise to a stirred solution of exo-3-(5-chloropyrid-3-yl)-endo-3-cyano-8-(O,O-diethylphosphonomethyl)-8-azabicyclo[3.2.1]octane (0.56 g) in dichloromethane (30 ml) at 0° C. After 30 minutes the mixture was allowed to warm to room temperature. After 7 hours trimethylsilyl bromide (0.8 ml) was added, after 23 hours more trimethylsilyl bromide (0.5 ml) was added and after 18 hours further trimethylsilyl bromide (0.5 ml) was added. After 24 hours the mixture was evaporated under reduced pressure, water added and the mixture filtered. After 10 minutes the filtrate was azeotroped with methanol/toluene to give exo-3-(5-chloropyrid-3-yl)-endo-3-cyano-8-phosphonomethyl-8-azabicyclo[3.2.1]octane (0.49 g) m.p. 242–245° C.

EXAMPLE 78

This example illustrates the preparation of exo-3-(5-chloropyrid-3-yl)-endo-3-cyano-8-(2-cyanoethyl)-8-azabicyclo[3.2.1]octane.

3-Bromopropionitrile (0.174 ml) was added to exo-3-(5-chloropyrid-3-yl)-endo-3-cyano-8-azabicyclo[3.2.1]octane (0.40 g) and potassium carbonate (0.45 g) in ethanol (10 ml) and the mixture heated under reflux for 16 hours. 3-Bromopropionitrile (0.13 ml) was added and the mixture refluxed for 3 hours and allowed to cool to room temperature. Water was added and the mixture extracted with dichloromethane (x3). The combined extracts were washed with brine, dried ($MgSO_4$) and evaporated under reduced pressure. Chromatography [$SiO_2$; dichloromethane:methanol (100:0) to (98:2] gave exo-3-(5-chloropyrid-3-yl)-endo-3-cyano-8-(2-cyanoethyl)-8-azabicyclo[3.2.1]octane (0.343 g).

EXAMPLE 79

This example illustrates the preparation of exo-3-(5-chloropyrid-3-yl)-endo-3-cyano-8-(1,1-dimethyl-2,2,2-trifluoroethyl)-8-azabicyclo[3.2.1]octane.

4Å Molecular sieves (1.0 g) were added to a suspension of exo-3-(5-chloropyrid-3-yl)-endo-3-cyano-8-azabicyclo[3.2.1]octane hydroperchlorate (3.42 g) in acetone (30 ml) and the mixture heated under reflux for 5 hours. The mixture was then allowed to cool to room temperature and filtered to give exo-3-(5-chloropyrid-3-yl)-endo-8-isopropylene-8-azabicyclo[3.2.1]octanium perchlorate (0.279 g).

Trimethyl(trifluoromethyl)silane (5.2 ml of a 0.5M solution in tetrahydrofuran) was added to a suspension of exo-3-(5-chloropyrid-3-yl)-endo-3-cyano-8-isopropylene-8-azabicyclo[3.2.1]octanium perchlorate (0.50 g) in tetrahydrofuran (5 ml). Cesium fluoride (0.39 g) was added and the mixture placed in an ultrasound bath for 2.5 hours. The mixture was then added to water and the resulting mixture extracted with dichloromethane (x3). The combined extracts were washed with brine, dried ($MgSO_4$) and evaporated under reduced pressure. Chromatography [$SiO_2$; dichloromethane:methanol (97:3] followed by preparative thin layer chromatography [$SiO_2$; dichloromethane:methanol (98:2)] gave exo-3-(5-chloropyrid-3-yl)-endo-3-cyano-8-(1,1-dimethyl-2,2,2-trifluoroethyl)-8-azabicyclo[3.2.1]octane (0.02 g).

EXAMPLE 80

This example illustrates the preparation of exo-3-(5-(2,2,2-trifluoroethoxy)pyrid-3-yl)-endo-3-cyano-8-methyl-8-azabicyclo[3.2.1]octane.

Sodium (0.46 g) was added portionwise to a solution of 2,22,-trifluoroethyl (2.3 ml) in N-methylpyrrolidinone (20 ml) under nitrogen. Tetraphenylphosphonium bromide (0.05 g) and exo-3-(5-chloropyrid-3-yl)-endo-3-cyano-8-methyl-8-azabicyclo[3.2.1]octane (2.6 g) were added and the mixture heated at 110° C. for 18 hours and 140° C. for 5 hours. Sodium (0.6 g) was added to a solution of 2,22,-trifluoroethyl (3 ml) in N-methylpyrrolidinone (5 ml) and after 30 minutes the resulting mixture was added to the reaction mixture. After 6 hours at 140° C. the mixture was cooled to room temperature and added to water. The mixture was extracted with diethyl ether (x2) and the combined extracts were washed with water, dried ($MgSO_4$) and evaporated under reduced pressure. The resulting mixture was filtered [$SiO_2$; dichloromethane:methanol (95:5)] and chromatographed [$SiO_2$; dichloromethane:methanol (95:5] to give exo-3-(5-(2,2,2-trifluoroethoxy)pyrid-3-yl)-endo-3-cyano-8-methyl-8-azabicyclo[3.2.1]octane (0.065 g, 80% pure).

EXAMPLE 81

This example illustrates the preparation of exo-3-(5-chloropyrid-3-yl)-endo-3-cyano-8-(1-cyanoethyl)-8-azabicyclo[3.2.1]octane.

exo-3-(5-Chloropyrid-3-yl)-endo-3-cyano-8-azabicyclo[3.2.1]octane (0.50 g), 2-bromopropionitrile (2 ml) and potassium carbonate (0.50 g) were refluxed in ethanol (5 ml). After 24 hours the mixture was cooled to room temperature, water added and the mixture extracted with dichloromethane (x3). the combined extracts were washed with brine, dried (MgSO$_4$) and evaporated under reduced pressure. Chromatography [SiO$_2$; dichloromethane:methanol (100:0) to (98:2)] followed by chromatography [SiO$_2$; ethyl acetate:hexane (80:20)] and preparative thin layer chromatography [Al$_2$O$_3$; ethyl acetate:hexane (40:60)] gave exo-3-(5-chloropyrid-3-yl)-endo-3-cyano-8-(1-cyanoethyl)-8-azabicyclo[3.2.1]octane (0.044 g, 80% pure).

EXAMPLE 82

This example illustrates the preparation of exo-3-(5-phenylpyrid-3-yl)-endo-3-cyano-8-(vinyloxycarbonyl)-8-azabicyclo[3.2.1]octane.

Vinyl choroformate (2.17 ml) was added a solution of exo-3-(5-iodopyrid-3-yl)-endo-3-cyano-8-methyl-8-azabicyclo[3.2.1]octane (3.0 g) in tetrahydrofuran (20 ml) at 0° C. The mixture was then heated under reflux for 5 hours and then stand at room temperature overnight. Water was then added and the mixture extracted with dichloromethane (x3). The combined extracts were washed with water and brine, dried (MgSO$_4$) and evaporated under reduced pressure. Chromatography [SiO$_2$;dichloromethane:methanol (98:2)] gave exo-3-(5-iodopyrid-3-yl)-endo-3-cyano-8-(vinyloxycarbonyl)-8-azabicyclo[3.2.1]octane (3.64 g).

Tetrakis(triphenylphosphine)palladium(0) (0.042 g) was added to a stirred solution of exo-3-(5-iodopyrid-3-yl)-endo-3-cyano-8-(vinyloxycarbonyl)-8-azabicyclo[3.2.1]octane (0.50 g) in toluene (2 ml). To this mixture was added 2M sodium carbonate solution (1.22 ml) and phenylboronic acid (0.16 g) in ethanol (0.5 ml) and the mixture heated under reflux. After 2 hours the mixture was cooled to room temperature, water added and the mixture extracted with ethyl acetate (x3). The combined extracts were washed with brine, dried (MgSO$_4$) and evaporated under reduced pressure. Chromatography [SiO$_2$; ethyl acetate:hexane (45:55)] gave exo-3-(5-phenylpyrid-3-yl)-endo-3-cyano-8-(vinyloxycarbonyl)-8-azabicyclo[3,2.1]octane (0.33 g).

EXAMPLE 83

This example illustrates the preparation of exo-3-(5-phenylpyrid-3-yl)-endo-3-cyano-8-azabicyclo[3.2.1]octane.

Concentrated hydrochloric acid (0.5 ml) was added to a solution of exo-3-(5-phenylpyrid-3-yl)-endo-3-cyano-8-(vinyloxycarbonyl)-8-azabicyclo[3.2.1]octane (0.30 g) in methanol (10 ml) and the mixture heated under reflux. After 5 hours the mixture was allowed to stand at room temperature for 4 days and then heated under reflux for 5 hours. The mixture was then allowed to cool to room temperature, basified with saturated sodium bicarbonate solution and extracted with dichloromethane (x3). The combined extracts were washed with brine and extracted with 2M hydrochloric acid (x2). The acidic extracts were basified and re-extracted with dichloromethane (x3). The combined organic extracts were washed with brine, dried (MgSO$_4$) and evaporated under reduced pressure to give exo-3-(5-phenylpyrid-3-yl)-endo-3-cyano-8-azabicyclo[3.2.1]octane (0.20 g).

EXAMPLE 84

This example illustrates the preparation of exo-3-(5-methylpyrid-3-yl)-endo-3-cyano-8-(vinyloxycarbonyl)-8-azabicyclo[3.2.1]octane.

Methyllithium (8.7 ml of a 1.4M solution in diethyl ether) was added dropwise to a stirred suspension of copper(I) iodide (1.16 g) in diethyl ether (10 ml) at 0° C. under nitrogen. After 45 minutes exo-3-(5-iodopyrid-3-yl)-endo-3-cyano-8-(vinyloxycarbonyl)-8-azabicyclo[3.2.1]octane (0.50 g) in diethyl ether (5 ml) was added. After 5 days at room temperature water was added and the mixture extracted with ethyl acetate (x3). The combined extracts were washed with brine, dried (MgSO$_4$) and evaporated under reduced pressure. Chromatography [SiO$_2$; ethyl acetate;hexane (60:40] gave exo-3-(5-methylpyrid-3-yl)-endo-3-cyano-8-(vinyloxycarbonyl)-8-azabicyclo[3.2.1]octane (0.085 g).

EXAMPLE 85

This example illustrates the preparation of exo-3-(5-chloropyrid-3-yl)-endo-3-cyano-8-(2-cyanoprop-2-yl)-8-azabicyclo[3.2.1]octane.

Sodium cyanide (0.069 g) was added to a stirred solution of exo-3-(5-chloropyrid-3-yl)-endo-3-cyano-8-isopropylene-8-azabicyclo[3.2.1]octanium perchlorate (0.50 g) in acetonitrile (5 ml) at room temperature under nitrogen. After 4 hours the mixture was allowed to stand at room temperature over the weekend, water added and the mixture extracted with dichloromethane (x3). The combined extracts were washed with brine, dried (MgSO$_4$) and evaporated under reduced pressure to give exo-3-(5-chloropyrid-3-yl)-endo-3-cyano-8-(2-cyanoprop-2-yl)-8-azabicyclo[3.2.1]octane (0.38 g, 90% pure).

EXAMPLE 86

This example illustrates the preparation of exo-3-(5-(ethoxycarbonyl)pyrid-3-yl)-endo-3-cyano-8-(vinyloxycarbonyl)-8-azabicyclo[3.2.1]octane.

Potassium carbonate (0.205 g) and bis(triphenylphosphine)palladium(II) chloride (0.026 g) were added to a stirred solution of exo-3-(5-iodopyrid-3-yl)-endo-3-cyano-8-methyl-8-azabicyclo[3.2.1]octane (0.50 g) in ethanol (10 ml) under nitrogen. The reaction vessel was then flushed with carbon monoxide, triethylamine (3 drops) added and the mixture heated under reflux. After 3 hours the mixture was cooled to room temperature, water and brine added and the mixture extracted with ethyl acetate (x3). The combined extracts were dried (MgSO$_4$), evaporated under reduced pressure and chromatographed [SiO$_2$; ethyl acetate-:hexane (35:65)] to give exo-3-(5-ethoxycarbonyl)pyrid-3-yl)-endo-3-cyano-8-(vinyloxycarbonyl)-8-azabicyclo[3.2.1]octane (0.29 g).

Confirmation of the structural identify of the compounds prepared in Examples 20 to 106 was obtained by proton magnetic resonance spectroscopy. The results are set out in the following table.

EXAMPLE $^1$H NMR (270 MHz), in CDCl$_3$ unless otherwise stated 1 8.81 (1H, d), 8.56 (1H, dd), 7.85 (1H, dt), 7.30 (1H, dd), 3.44 (2H, m), 2.45–2.15 (8H, m) and 2.33 3H, s).

2 8.80 (1H, d), 8.55 (1H, dd), 7.85 (1H, m), 7.30 (1H, m), 4.55 (2H, dt), 3.4 (2H, m), 2.70 (2H, dt) and 2.4–2.1 (8H, m).

3 7.09 (2H, m), 6.75 (1H, m), 3.31 (2H, m), 2.4–2.1 (8H, m) and 2.35 (3H, s).

4 8.80 (1H, d), 8.54 (1H, dd), 7.83 (1H, dt), 7.29 (1H, dd), 3.40 (2H, m), 2.4–2.0 (10H, m), 1.48 (2H, hex) and 0.91 (3H, s).

5 7.53 (2H, m), 7.4–7.2 (8H, m), 3.59 (2H, s), 3.36 (2H, m) and 2.5–2.15 (8H, m).
6 8.82 (1H, d), 8.58 (1H, dd), 7.86 (1H, dt), 7.4–7.2 (6H, m), 3.59 (2H, s), 3.39 (2H, m) and 2.45–2.15 (8H, m).
7 8.80 (1H, d), 8.56 (1H, dd), 7.84 (1H, dt), 7.31 (1H, dd), 3.50 (2H, t), 3.48 (2H, m), 3.36 (3H, s), 2.61 (2H, t) and 2.4–2.05 (8H, m).
8 8.61 (1H, m), 7.68 (2H, m), 7.20 (1H, m), 3.34 (2H, m), 2.64 (2H, m), 2.5–2.1 (6H, m) and 2.37 (3H, s).
9 8.94 (1H, d), 8.59 (1H, t), 8.53 (1H, d), 3.35 (2H, m), 2.65–2.55 (2H, m), 2.4–2.1 6H, m) and 2.36 (3H, m).
10 8.82 (1H, s), 8.54 (1H, s), 3.37 (2H, m), 2.54 (2H, dd), 2.4–2.1 (6H, m) and 2.35 (3H, s).
11 7.78 (1H, d), 7.55 (1H, d), 3.40 (2H, m), 2.70 (2H, m), 2.5–2.1 (6H, m) and 2.37 (3H, s).
12 8.49 (1H, d), 7.95 (1H, d), 3.34 (2H, m), 2.4–2.15 (8H, m) and 2.35 (3H, s).
13 8.81 (1H, d), 8.56 (1H, dd), 7.84 (1H, dt), 7.31 (1H, dd), 3.72 (3H, s), 3.50 (2H, m), 3.22 (2H, s), 2.5–2.3 (6H, m) and 2.2–2.1 (2H, m).
14 8.89 (1H, m), 8.60 (1H, dd), 7.87 (1H, dt), 7.35 (1H, dd), 4.54 (2H, m), 4.50 (2H, s), 3.22 (3H, s) and 2.6–2.25 (8H, m).
15 8.59 (1H, d), 7.81 (1H, dd), 7.34 (1H, d), 3.33 (2H, m), 2.4–15 (2H, m) and 2.35 (3H, s).
16 8.69 (1H, d), 8.51 (1H, d), 7.82 (1H, t), 3.42 (2H, m), 2.4–2.0 (10H, m), 1.5–1.2 (8H, m) and 0.89 (3H, m).
17 8.70 (1H, d), 8.52 (1H, d), 7.83 (1H, t) 5.88 (1H, m), 5.18 (2H, m), 3.42 (2H, m), 3.02 (2H, m) and 2.4–2.05 (8H, m).
18 8.70 (1H, d), 8.55 (1H, d), 7.80 (1H, t), 3.50 (2H, m), 2.90 (2H, q), 2.5–2.2 (6H, m) and 2.10 (2H, m).
19 8.74 (1H, d), 8.61 (1H, d), 8.00 (1H, t), 3.35 (1H, m), 2.4–2.15 (8H, m) and 2.33 (3H, s).
20 9.03 (1H, d), 8.82 (1H, d), 8.15 (1H, t), 3.36 (1H, m), 2.4–2.2 (8H, m) and 2.35 (3H, s).
21 8.40 (1H, d), 8.21 (1H, d) 7.34 (1H, t), 4.10 (2H, q), 3.31 (2H, m), 2.4–2.15 (8H, m), 3.32 (3H, s) and 1.44 (3H, t).
22 8.70 (1H, d), 8.50 (1H, d), 7.80 (1H, t), 3.70 (2H, m), 2.65 (1H, m), 2.35 (2H, m), 2.25 (4H, m), 2.05 (2H, m) and 1.05 (6H, d).
23 7.47 (2H, s), 3.32 (2H, m), 2.35–2.15 (8H, m) and 2.32 (3H, s).
24 8.39 (1H, d), 7.51 (1H, d), 7.40 (1H, dd), 3.32 (2H, m), 2.4–2.1 (8H, m) and 2.32 (3H, s).
25 8.61 (2H, m), 7.49 (2H, m), 3.33 (2H, m), 2.4–2.1 (8H, m) and 2.32 (3H, s).
28 8.69 (1H, d), 8.51 (1H, d), 7.81 (1H, t), 4.35 (1H, dd), 3.41 (2H, m), 3.00 (2H, dt) and 2.4–2.1 (8H, m).
27 8.59 (2H, m), 7.98 (1H, d), 7.72 (1H, d), 5.55 (1H, d), 4.36 (1H, m), 4.25 (1H, m), 2.7–2.2 (8H, m).
28 8.65 (1H, d), 8.55 (1H, d), 7.75 (1H, t), 4.95 (1H, m), 4.40 (1H, m), 2.65–2.1 (8H, m) and 2.15 (3H, s).
29 [in DMSO] 8.79 (1H, brs), 8.70 (1H, d), 8.64 (1H, brs), 8.61 (1H, d), 4.16 (2H, m), 2.7–2.6 (2H, m), 2.45–2.25 (4H, m), and 2.15–2.0 (2H, m).
30 8.67 (1H, d), 8.49 (1H, d), 7.80 (1H, f), 3.79 (2H, m), 2.4–2.15 (6H, m), 2.0–1.9 (2H, m) and 1.09 (9H, s).
31 9.56 (1H, s), 8.75 (1H, d), 8.55 (1H, d), 7.89 (1H, t), 7.55–7.3 (5H, m), 3.60 (1H, m), 3.38 (1H, m), 2.6–1.9 (8H, m) and 1.54 (3H, s).
32 8.72 (1H, d), 8.53 (1H, d), 7.89 (1H, t), 7.53 (2H, m), 7.35–7.2 (3H, m), 6.11 (1H, dd), 5.29 (1H, d), 5.19 (1H, d), 3.63 (1H, m), 3.54 (1H, m), 2.45–1.9 (8H, m) and 1.51 (3H, s).
33 8.69 (1H, d), 8.52 (1H, d), 7.82 (1H, t), 7.54 (2H, m), 7.4–7.25 (3H, m), 3.90 (1H, m), 3.70 (1H, m), 3.65 (1H, d), 3.31 (1H, m), 2.5–2.0 (8H, m) and 1.49 (3H, m).
34 8.60 (1H, d), 8.50 (1H, d), 7.71 (1H, t), 7.4–7.25 (5H, m), 3.40 (1H, m), 3.32 (1H, m), 2.82 (1H, t), 2.66 (1H, t), 2.3–1.95 (8H, m) and 1.74 (3H, d).
35 8.70 (1H, d), 8.54 (1H, d), 7.85 (1H, t), 7.50 (2H, m), 7.4–7.25 (3H, m), 4.31 (1H, d), 4.19 (1H, d), 3.85 (1H, m), 2.34 (1H, m), 2.5–2.15 (8H, m), 2.00 (3H, s) and 1.56 (3H, s).
36 8.64 (1H, d), 8.56 (1H, d), 8.20 (1H, s), 7.77 (1H, t), 4.86 (1H, m), 4.32 (1H, m) and 2.6–2.1 (8H, m).
37 8.69 (1H, d), 8.52 (1H, d), 7.85 (1H, t), 4.11 (2H, m), 3.65 (2H, hept), 2.55–2.1 (8H, m) and 1.30 (12H, d).
38 8.62 (1H, d), 8.52 (1H, d), 7.75 (1H, t), 4.26 (2H, m), 2.5–2.15 (8H, m) and 1.40 (9H, s).
39 8.71 (1H, d), 8.53 (1H, d), 7.84 (1H, t), 7.4–7.2 (5H, m), 3.71 (1H, m), 3.49 (1H, q), 3.28 (1H, m), 2.4–2.05 (8H, m) and 1.30 (3H, d).
40 8.20 (1H, d), 8.00 (1H, d), 7.11 (1H, t), 3.76 (2H, brs), 3.32 (2H, m), 2.4–2.1 (8H, m) and 2.32 (3H, s).
41 8.62 (1H, d), 8.56 (1H, d), 8.22 (1H, t), 7.46 (1H, brs), 3.35 (2H, m), 2.4–2.2 (8H, m), 2.35 (3H, s) and 2.21 (3H, s).
42 8.69 (1H, d), 8.54 (1H, d), 7.81 (1H, t), 7.55–7.35 (5H, m), 4.38 (1H, s), 3.94 (1H, m), 3.29 (1H, m) and 2.6–2.1 (8H, m).
43 8.69 (1H, d), 8.55 (1H, d), 7.81 (1H, t), 7.45–7.3 (5H, m), 6.91 (1H, m), 5.70 (1H, m), 3.96 (1H, s), 3.60 (1H, m), 3.35 (1H, m), 2.5–2.2 (8H, m) and 2.05–1.9 (2H, m).
44 8.77 (2H, m), 8.16 (1H, t), 3.32 (2H, m), 2.4–2.1 (8H, m) and 2.32 (3H, s).
45 9.02 (1H, d), 8.83 (1H, m), 8.07 (1H, m), 3.36 (2H, m) and 2.4–2.05 (11H, m).
46 [in DMSO] 8.72 and 8.62 (1H, m), 8.58 (1H, m), 8.14 and 7.86 (1H, m), 5.39 (1H, m), 4.20 (1H, m) 2.7–2.0 (8H, m).
47 8.65 (1H, d), 8.58 (1H, d), 7.78 (1H, t), 4.51 (2H, m), 2.6–2.2 (8H, m).
48 8.69 (1H, d), 8.52 (1H, d,), 7.81 (1H, t), 5.85 (1H, tt), 3.45 (1H, m), 2.71 (2H, dt) and 2.5–2.0 (8H, m).
49 8.69 (1H, d), 8.52 (1H, d), 7.82 (1H, t), 7.35–7.15 (5H, m), 3.45 (2H, m), 2.79 (2H, m), 2.61 (2H, m) and 2.4–2.05 (8H, m).
50 8.39 (1H, m), 8.05 (1H, m), 7.59 (1H, m), 3.43 (2H, m) 2.5–2.1 (8H, m) and 2.40 (3H, s).
51 8.70 (1H, d), 8.52 (1H, d), 7.83 (1H, t), 7.4–7.2 (5H, m), 3.57 (2H, s), 3.40 (2H, m) and 2.45–2.2 (8H, m).
52 8.63 (1H, d), 8.50 (1H, d), 7.77 (1H, t), 3.60 (2H, m), 3.42 (2H, m) and 2.5–2.2 (8H, m).
53 8.71 (1H, d), 8.53 (1H, d), 8.10 (1H, t), 7.90 (2H, m), 7.39 2H, m), 3.45 (2H, m), 3.30 (2H, m) and 2.4–2.2 (8H, m).
54 8.69 (1H, d), 8.53 (1H, d), 7.83 (1H, t), 7.42 (1H, dd), 7.22 (1H, m), 7.09 (1H, t), 3.50 (2H, s), 3.36 (2H, m) and 2.45–2.15 (8H, m).
55 8.71 (1H, d), 8.52 (2H, m), 7.86 (1H, t), 7.69 (1H, dt), 7.54 (1H, d), 7.19 (1H, m), 3.73 (2H,s), 3.43 (2H, m) and 2.5–2.2 (8H, m).
56 8.70 (1H, d), 8.52 (1H, d), 7.85 (1H, t), 7.00 (1H, s), 3.66 (2H, s), 3.49 (2H, m), 2.70 (3H, s) and 2.45–2.15 (8H, m).
57 8.61 (1h, d), 8.52 (1H, d), 7.78 (1H, t), 3.33 (2H, m), 3.29 (2H, s), 2.5–2.1 (8H, m), 2.38 (3H, s) and 2.32 (3H, s).
58 8.70 (1H, d), 8.52 (1H, d), 7.83 (1H, t), 6.74 (1H, d), 6.65 (1H, d), 3.65 (2H, s), 3.46 (2H, m) and 2.45–2.1 (8H, m).
59 8.65 (1H, d), 8.50 (1H, d), 7.80 (1H, t), 3.94 (2H,s), 3.55 (2H, m) and 2.5–2.25 (8H, m).
60 8.65 (1H, d), 8.41 (1H, d), 7.60 (1H, dt), 3.44 (2H, m), 2.4–2.15 (8H, m) and 2.35 (3H, s).
61 8.69 (2H, m), 7.84 (1H, t), 7.10 (2H, m), 6.40 (2H, m), 3.34 (2H, m), 2.4–2.15 (8H, m) and 2.33 (3H, s).
62 8.79 (1H, d), 8.75 (1H, d), 8.05 (1H, m), 4.74 (1H, d), 4.31 (1H, d), 3.94 (2H, q), 3.40 (2H, m), 2.5–2.2 (11H, m) and 1.44 (3H, t).

63 9.09 (1H, d), 8.99 (1H, d), 8.39 (1H, t), 3.37 (2H, m), 2.69 (3H, s), 2.45–2.15 (8H, m) and 2.34 (3H, s).

64 8.76 (1H, d), 8.62 (1H, d), 7.94 (1H, m), 3.34 (2H, m), 3.24 (1H, s), 2.45–2.15 (8H, m) and 2.35 (3H, s).

65 8.80 and 8.70 (1H, m), 8.29 (1H, m), 7.95 (1H, m), 7.71 (1Hm), 7.56 (1H, m), 7.4–7.1 (3H, m), 5.65 and 5.29 (1H, m), 4.91 and 4.75 (1H, m), 4.30 and 4.11 (1H, m), 3.30 (1H, m), 2.8–2.0 (8H, m) and 1.73 and 1.62 (3H, m).

66 8.61 (1H, d), 8.52 (1H, d), 7.79 (1H, t), 7.5–7.15 (5H, m), 3.01 (1H, m), 2.91 (1H, m), 2.79 (1H, m), 2.39 (2H, m), 2.3–1.6 (12H, m), 1.09 (3H, d) and 0.91 (3H, d).

67 8.69 (1H, d), 8.52 (1H, d), 7.81 (1H, t), 3.55 (2H, t), 3.55 (2H, m), 3.35 (2H, s) and 2.5–2.1 (8H, m).

68 8.69 (1H, d), 8.52 (1H, d), 7.81 (1H, t), 4.20 (2H, m), 3.61 (1H, m), 3.49 (1H, m), 3.23 (1H, q), 2.45–2.0 (8H, m), 1.31 (3H, d) and 1.29 (3H, t).

69 8.50 (1H, d), 8.35 (1H, d), 7.7–7.5 (2H, m), 6.40 (2H, dd), 6.25 (1H, dd), 4.70 (2H, m), 2.6–2.5 (2H, m) 2.45–2.20 (6H, m).

70 8.51 (1H, d), 8.49 (1H, d), 7.70 (1H, t), 4.45 (2H, m), 2.6–2.5 (4H, m) and 2.4–2.2 (4H, m).

71 8.70 (1H, d), 8.55 (1H, d), 7.85 (1H, t), 4.25 (2H, m) and 2.6–2.2 (8H, m).

72 8.29 (1H, d), 8.10 (1H, d), 7.90 (1H, m), 4.15 (2H, m) 2.6–2.25 (8H, m).

73 8.75, 8.65 and 8.50 (1H, m), 7.90 and 7.80 (1H, m), 3.80 and 3.70 (2H, m), 3.6 and 3.5 (3H, m), and 2.7–1.8 (8H, m).

74 8.65 (1H, d), 8.51 (1H, d), 7.80 (1H, t), 4.16 (2H, q), 3.41 (2H, m), 2.69 (2H, t), 2.48 (2H, t), 2.4–2.05 (8H, m) and 1.27 (3H, t).

75 8.76 (1H, m), 8.52 (1H, m), 7.98 (1H, m), 3.85 (2H, m), 3.01 (2H, t), 2.8–2.2 (10H, m).

76 8.64 (1H, d), 8.51 (1H, d), 7.80 (1H, t), 4.18 (4H, m), 3.60 (2H, m), 2.78 (2H, d), 2.45–2.05 (8H, m), and 1.36 (6H, m).

77 [in DMSO] 8.89 (1H, d), 8.62 (1H, d), 8.29 (1H, t), 4.50 (2H, m), 3.48 (2H, d) and 2.85–2.45 (8H, m).

78 8.69 (1H, d), 8.51 (1H, d), 7.80 (1H, t), 3.46 (2H, m), 2.64 (2H, m), 2.51 (2H, m) and 2.45–2.0 (8H, m).

79 9.65 (1H, d), 8.51 (1H, d), 7.79 (1H, t), 3.91 (2H, m), 2.45–2.2 (8H, m) and 1.28 (6H, s).

80 8.55 (1H, d), 8.3 (1H, d) 7.45 (1H, t), 3.35 (2H, m), 2.4–2.1 (8H, m) and 2.3 (3H, s).

81 8.69 (1H, d), 8.52 (1H, d), 7.81 (1H, t), 3.85 (1H, m), 3.60 (1H, m), 3.50 (1H, q), 2.5–2.1 (8H, m) and 1.51 (3H, d).

82 8.81 (1H, d), 8.71 (1H, d), 7.92 (1H, t), 7.6–7.35 (5H, m), 7.25 (1H, dd), 4.80 (1H, dd), 4.61 (2H, m), 4.49 (1H, dd) and 2.55–2.15 (8H, m).

83 8.79 (2H, m), 7.99 (1H, t), 7.6–7.35 (5H, m), 3.75 (2H, m), 2.55–2.2 (6H, m) and 2.05–1.85 (2H, m).

84 8.55 (1H, m), 8.40 (1H, m), 7.55 (1H, m), 7.23 (1H, dd), 4.80 (1H, dd), 4.59 (1H, m), 4.49 (1H, dd), 2.6–2.1 (8H, m) and 2.39 (3H, s).

85 8.64 (1H, d), 8.52 (1H, d), 7.70 (1H, t), 3.91 (1H, m), 2.55–215 (8H, m) and 1.52 (6H, s).

86 9.19 (1H, d), 8.90 (1H, d), 8.31 (1H, t), 7.24 (1H, dd), 4.82 (1H, dd), 4.63 (2H, m), 4.51 (1H, dd), 4.44 (2H, q), 2.6–2.2 (8H, m) and 1.43 (3H, t).

EXAMPLE 87

This Example illustrates an emulsifiable concentrate composition which is readily convertible by dilution with water into a liquid preparation suitable for spraying purposes. The concentrate has the following composition:

|  | % Weight |
| --- | --- |
| Compound No. 1 | 25.5 |
| SYNPERONIC NP13 | 2.5 |
| Calcium dodecylbenzenenesulphonate | 2.5 |
| AROMASOL H | 70 |

EXAMPLE 88

This Example illustrates an emulsifiable concentrate composition which is readily convertible by dilution with water into a liquid preparation suitable for spraying purposes. The concentrate has the following composition:

|  | % Weight |
| --- | --- |
| Compound No. 5 | 50.0 |
| SYNPERONIC NP13 | 6.0 |
| Calcium dodecylbenzenenesulphonate | 4.0 |
| AROMASOL H | 40.0 |

EXAMPLE 89

This Example illustrates an emulsifiable concentrate composition which is readily convertible by dilution with water into a liquid preparation suitable for spraying purposes. The concentrate has the following composition:

|  | % Weight |
| --- | --- |
| Compound No. 9 | 1.0 |
| SYNPERONIC OP10 | 3.0 |
| Calcium dodecylbenzenenesulphonate | 2.0 |
| AROMASOL H | 94.0 |

EXAMPLE 90

This Example illustrates a wettable powder composition which is readily convertible by dilution with water into a liquid preparation suitable for spraying purposes. The wettable powder has the following composition:

|  | % Weight |
| --- | --- |
| Compound No. 13 | 25.0 |
| Silica | 25.0 |
| Sodium lignosulphonate | 5.0 |
| Sodium lauryl sulphate | 2.0 |
| Kaolinite | 43.0 |

EXAMPLE 91

This Example illustrates a wettable powder composition which is readily convertible by dilution with water into a liquid preparation suitable for spraying purposes. The wettable powder has the following composition:

| | % Weight |
|---|---|
| Compound No. 17 | 1.0 |
| Sodium lignosulphonate | 5.0 |
| Sodium lauryl sulphate | 2.0 |
| Kaolinite | 92.0 |

EXAMPLE 92

This Example illustrates a wettable powder composition which is readily convertible by dilution with water into a liquid preparation suitable for spraying purposes. The wettable power has the following composition:

| | % Weight |
|---|---|
| Compound No. 21 | 40.0 |
| Silica | 40.0 |
| Calcium lignosulphonate | 5.0 |
| Sodium lauryl sulphate | 2.0 |
| Kaolinite | 13.0 |

EXAMPLE 93

This Example illustrates a dusting powder which may be applied directly to plants or other surfaces and comprises 1% by weight of Compound No. 25 and 99% by weight of talc.

EXAMPLE 94

This Example illustrates a concentrated liquid formulation suitable for application by ultra low volume techniques after mixing with paraffinic diluents.

| | % Weight |
|---|---|
| Compound No. 29 | 90.0 |
| SOLVESSO 200 | 10.0 |

EXAMPLE 95

This Example illustrates a concentrated liquid formulation suitable for application by ultra low volume techniques after mixing with paraffinic diluents.

| | % Weight |
|---|---|
| Compound No. 33 | 25.0 |
| SOLVESSO 200 | 75.0 |

EXAMPLE 96

This Example illustrates a concentrated liquid formulation suitable for application by ultra low volume techniques after mixing with paraffinic diluents.

| | % Weight |
|---|---|
| Compound No. 37 | 10.0 |
| SOLVESSO 200 | 90.0 |

EXAMPLE 97

This Example illustrates a liquid formulation suitable for application (undiluted) by ultra low volume techniques.

| | % Weight |
|---|---|
| Compound No. 41 | 15 |
| Cotton seed oil | 50 |
| SOLVESSO 200 | 35 |

EXAMPLE 98

This Example illustrates a capsule suspension concentrate which is readily convertible by dilution with water to form a preparation suitable for application as an aqueous spray.

| | % Weight |
|---|---|
| Compound No. 45 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL) | 0.1 |
| Water | 76.4 |

EXAMPLE 99

This Example illustrates a capsule suspension concentrate which is readily convertible by dilution with water to form a preparation suitable for application as an aqueous spray.

| | % Weight |
|---|---|
| Compound No. 49 | 1.0 |
| Alkylbenzene solvent (e.g. AROMASOL H) | 10.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL) | 0.1 |
| Water | 80.4 |

EXAMPLE 100

A ready for use granular formulation:

| | % Weight |
|---|---|
| Compound No. 4 | 0.5 |
| SOLVESSO 200 | 0.2 |
| nonylphenol ethoxylate | 0.1 |

-continued

| | % Weight |
|---|---|
| (eg Synperonic NP8) | |
| Calcium carbonate granules (0.3–0.7 mm) | 99.2 |

EXAMPLE 101

An aqueous suspension concentrate:

| | % Weight |
|---|---|
| Compound No. 8 | 5.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 102

A ready for use dust (D.P.) made from a concentrate Concentrate:

| | % Weight |
|---|---|
| Compound No. 12 | 10 |
| Silica | 20 |
| Magnesium Carbonate | 70 |
| Dust Example containing 1% active ingredient: | |
| Above concentrate | 10 |

EXAMPLE 103

This Example illustrates a ready for use granule formulation.

| | % Weight |
|---|---|
| Compound No. 16 | 5 |
| Synperonic NP8 | 2 |
| Pumice granules (20/40 BS Mesh) | 93 |

EXAMPLE 104

This Example illustrates a water dispersible granule formulation.

| | % Weight |
|---|---|
| Compound No. 20 | 5 |
| Silica | 5 |
| Sodium lignosulphate | 10 |

-continued

| | % Weight |
|---|---|
| Sodium dioctylsulphosuccinate | 5 |
| Sodium acetate | 10 |
| Montmorillonite powder | 65 |

EXAMPLE 105

This Example illustrates the insecticidal properties of the compounds of Formula I. The activity of the the compounds of Formula I was determined using a variety of pests. The pests were treated with a liquid composition containing 500 parts per million (ppm) by weight of the compound unless otherwise stated. The compositions were made by dissolving the compound in acetone and ethanol (50:50) mixture and diluting the solutions with water containing 0.05% by weight of a wetting agent sold under the trade name "SYNPERONIC" NP8 until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a footstuff on which the pests feed, and treating either or both the medium and the pests with the compositions. The mortality of the pests was then assessed at periods usually varying from two to give days after the treatment.

The results of the tests against peach aphid (*Myzus persicae*) are presented in Table II. The results indicate a grading of mortality (score) designated as A, B or C wherein C indicates less than 40% mortality, B indicates 40–79% mortality and A indicates 80–100% mortality; "–" indicates that either the compound was not tested or no meaningful result was obtained. In this test Chinese cabbage leaves were infested with aphids, the infested leaves were sprayed with the test composition, and the mortality assessed after 3 days.

Information regarding the pest species, the support medium or food, and the type and duration of the test is given in Table III. The pest species is designated by a letter code.

TABLE H

| Comp'd No | Score | Comp'd No | Score | Comp'd No | Score | Comp'd No | Score |
|---|---|---|---|---|---|---|---|
| 1 | A | 2 | A | 3 | A | 4 | A |
| 5 | A | 6 | C | 7 | C | 8 | A |
| 9 | A | 10 | A | 11 | A | 12 | A |
| 13 | B | 14 | A | 15 | A | 16 | C |
| 17 | C | 18 | A | 19 | C | 20 | C |
| 21 | A | 22 | A | 23 | A | 24 | A |
| 25 | A | 26 | B | 27 | A | 28 | C |
| 29 | B | 30 | A | 31 | C | 32 | A |
| 33 | A | 34 | A | 35 | A | 36 | A |
| 37 | A | 38 | A | 39 | C | 40 | A |
| 41 | A | 42 | A | 43 | A | 44 | A |
| 45 | C | 46 | A | 47 | A | 48 | A |
| 49 | A | 50 | A | 51 | A | 52 | C |
| 53 | A | 54 | A | 55 | A | 56 | A |
| 57 | A | 58 | C | 59 | A | 60 | A |
| 61 | A | 62 | A | 63 | C | 64 | A |
| 65 | C | 66 | C | 67 | A | 68 | A |
| 69 | A | 70 | A | 71 | A | 72 | A |
| 73 | C | 74 | A | 75 | A | 76 | A |
| 77 | A | 78 | A | 79 | A | 80 | A |
| 81 | A | 82 | A | 83 | A | 84 | A |

TABLE H-continued

| Comp'd No | Score | Comp'd No | Score | Comp'd No | Score | Comp'd No | Score |
|---|---|---|---|---|---|---|---|
| 85 | A | 86 | A | 87 | A | 88 | A |
| 89 | C | 90 | A | 91 | A | 92 | A |
| 93 | A | 94 | C | 95 | A | 96 | A |
| 97 | C | 98 | A | 99 | A | 100 | A |
| 101 | A | 102 | A | 103 | A | 104 | A |
| 105 | B | 106 | A | 107 | A | 108 | A |
| 109 | A | 110 | A | 111 | A | 112 | B |
| 113 | A | 114 | A | 115 | A | 116 | A |
| 117 | A | 118 | A | 119 | A | 120 | A |
| 121 | A | 122 | A | 123 | A | 124 | A |
| 125 | A | 126 | C | 127 | — | 128 | A |
| 129 | A | 130 | A | 131 | A | 132 | A |
| 133 | A | 134 | A | 135 | A | 136 | C |
| 137 | C | 138 | A | 139 | A | 140 | A |
| 141 | A | 142 | A | 143 | A | 144 | A |
| 145 | A | 146 | A | 147 | A | 148 | B |
| 149 | A | 150 | A | 151 | A | 152 | A |
| 153 | A | 154 | B | 155 | A | 156 | A |
| 157 | C | 158 | A | 159 | A | 160 | A |
| 161 | A | 162 | C | 163 | C | 164 | A |
| 165 | A | 166 | A | 167 | A | 168 | A |
| 169 | A | 170 | B | 171 | A | 172 | A |
| 173 | A | 174 | A | 175 | A | 176 | A |
| 177 | A | 178 | A | 179 | A | 180 | A |
| 181 | A | 182 | A | 183 | A | 184 | A |
| 185 | A | 186 | A | 187 | C | 188 | A |
| 189 | A | 190 | — | 191 | A | 192 | A |
| 193 | A | 194 | A | 195 | A | 196 | A |
| 197 | A | 198 | A | 199 | A | 200 | A |
| 201 | A | 202 | A | 203 | A | 204 | A |
| 205 | A | 206 | A | 207 | A | 208 | A |
| 209 | A | 210 | A | 211 | A | 212 | A |
| 213 | A | 214 | A | 215 | A | 216 | — |
| 217 | A | 218 | A | 219 | — | 220 | A |
| 221 | A | 222 | C | 223 | C | 224 | — |
| 225 | A | 226 | — | 227 | A | 228 | A |
| 229 | A | 230 | A | 231 | A | 232 | A |
| 233 | A | 234 | A | 235 | A | 236 | A |
| 237 | A | 238 | A | 239 | A | 240 | A |
| 241 | A | 242 | A | 243 | A | 245 | A |
| 246 | A | 247 | A | 248 | A | 249 | A |
| 250 | A | 251 | A | 252 | A | 253 | A |
| 254 | A | 255 | A | 256 | A | 257 | A |
| 258 | A | 259 | A | 260 | A | 261 | A |
| 262 | A | 263 | A | 264 | A | 265 | A |
| 266 | A | 267 | A | 268 | A | 269 | A |
| 270 | A | 271 | A | 272 | A | 273 | A |
| 274 | A | 275 | A | 276 | A | 277 | A |
| 278 | A | 279 | A | 280 | A | 281 | A |
| 282 | A | 283 | A | 284 | A | 285 | A |
| 286 | A | 287 | A | 288 | A | 289 | A |
| 290 | A | 291 | — | 292 | A | 293 | A |
| 294 | A | 295 | — | 296 | A | 297 | A |
| 298 | A | 299 | A | 300 | A | 301 | A |
| 302 | A | 303 | — | 304 | A | 305 | — |
| 306 | — | 307 | — | 308 | — | 309 | A |
| 310 | A | 311 | A | 312 | A | 313 | A |
| 314 | A | 315 | A | 316 | A | 317 | A |
| 318 | A | 319 | A | 320 | A | 321 | A |

In tests against tobacco budworm (*Heliothis virescens*, larvae) the following compounds scored A or B.

Compounds 2, 8, 14, 18, 23, 66, 72, 95, 99, 102, 104, 120, 131, 156, 169, 170, 227, 229, 231, 234, 236, 243, 260, 262, 270, 274, 312.

In tests against root knot nematodes (*Meloidogyme incognita*) the following compounds scored A or B.

Compounds 36, 55, 71, 77, 94, 99, 120, 160, 207, 233, 237, 238, 253, 257, 271, 312, 317, 318.

In tests against red spider mite (*Tetranychus urticae*) the following compounds scored A or B.

Compounds 12, 13, 22, 23, 25, 34, 37, 39, 47, 53, 63, 64, 66, 87, 90, 99, 101, 106, 120, 135, 142, 186, 193, 195, 199, 201, 207, 208, 236, 237, 239, 245, 247, 249, 280, 283, 310 to 321.

In tests against Whitefly (*Bemesia tabaci*) the following compounds were particularly effective.

Compounds 33, 34, 36, 56, 64, 68, 69, 70, 72, 74, 76, 77, 81, 90, 93, 99, 227 to 275.

the chemical formulae referred to in the preceding description are set out below.

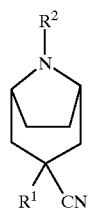

(I)

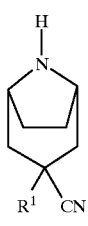

(II)

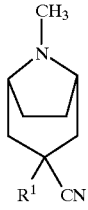

(III)

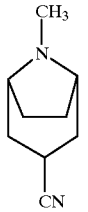

(IV)

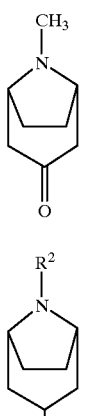

(V)

(VI)

-continued (VII)
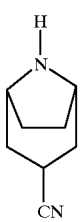

(VIII)
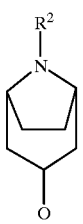

(IX)
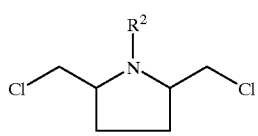

(X)
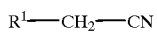

(XI)
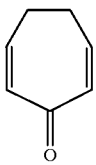

(XII)
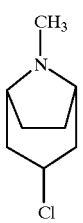

(XIII)
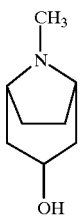

(A)
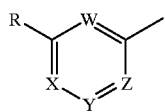

What is claimed is:

1. A compound of formula (I):

(I)

wherein $R^1$ represents a group of formula (A)

(A)
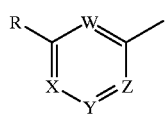

where each of W, X, Y and Z represents either a group CR or the nitrogen atom, provided that two of W, X, Y and Z represent the nitrogen atom and wherein each R present is independently selected from hydrogen, halogen atoms, cyano, amino, hydrazino, acylamino, hydroxy, alkyl, hydroxyalkyl, alkoxy, haloalkyl, haloalkoxy, alkenyl, alkenyloxy, alkoxyalkenyl, alkynyl, carboxylic acyl, alkoxycarbonyl, and aryl groups, said groups having up to 6 carbon atoms, and wherein $R^2$ represents hdyrogen cyano or a group selected from alkyl, aryl, aralkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, and dichlocarboxyl groups, said groups having from 1 to 15 carbon atoms, said groups being optionally substituted with one or more substituents selected from, halogen, cyano, carboxyl, carboxylic acryl, carbamyl, alkoxycarbonyl, alkoxy, alkylenedioxy, hydroxy, nitro, haloalkyl, alkyl, amino, acylamino, imidate and phosphonate groups; and acid addition salts, quaternary ammonium salts and N-oxides derived therefrom.

2. A compound according to claim 1 wherein $R^1$ represents a halo-substituted diazinyl group.

3. A compound according to claim 1 where $R^1$ represents an optionally halogen substituted pyridazinyl or pyrazinyl group and $R^2$ represents hydrogen, a $C_{1-4}$ alkyl, alkenyl, alkynyl, phenyl, or benzyl which may be optionally substituted with one or more alkyl, alkoxy, alkoxycarbonyl, cyano, optionally substituted alkane sulphonyl groups or halogen atoms; and alkoxycarbonyl, cyano, optionally substituted alkane sulphonyl groups or halogen atoms; and acid addition salts thereof.

4. A compound according to claim 1 wherein $R^2$ is a hydrogen or kaloalkyl, haloalkenyl or haloaralkyl group.

5. A compound according to claim 1 wherein $R^2$ is a haloalkyl or haloalkenyl group.

6. A compound according to claim 1 wherein $R^2$ is a fluoroalkyl or fluoroalkenyl group.

7. A compound according to claim 1 wherein $R^2$ is fluoroethyl, difluoroethyl or trifluoroethyl.

8. The compounding of claim 1, wherein $R^1$ is 6-chloropyridazin-3-yl and $R^2$ is methyl.

9. The compound of claim 1, wherein $R^1$ is 6-chloropyrazin-2-yl and $R^2$ is methyl.

10. The compound of claim 1, wherein $R^1$ is pyrazin-2-yl and $R^2$ is methyl.

11. The compound of claim 1, wherein $R^1$ is 2,6-dichloropyrimid-4-yl and $R^2$ is methyl.

12. The compound of claim 1, wherein $R^1$ is pyrimid-4-yl and $R^2$ is methyl.

13. The compound of claim 1, wherein $R^1$ is 5-bromopyrimid-4-yl and $R^2$ is methyl.

14. The compound of claim 1, wherein $R^1$ is 6-methoxypyrazin-2-yl and $R^2$ is methyl.

15. The compound of claim 1, wherein $R^1$ is ethynylpyrazin-2-yl and $R^2$ is methyl.

16. The compound of claim 1, wherein $R^1$ is 2-chloropyrimid-4-yl and $R^2$ is trifluoroethyl.

17. The compound of claim 1, wherein $R^1$ is 6-chloropyrazin-2-yl and $R^2$ is vinyloxycarbonyl.

18. The compound of claim 1, wherein $R^1$ is 6-chloropyrazin-2-yl and $R^2$ is hydrogen.

19. The compound of claim 1, wherein $R^1$ is 6-chloropyrazin-2-yl and $R^2$ is 3-chlorobenzyl.

20. The compound of claim 1, wherein $R^1$ is 6-chloropyrazin-2-yl and $R^2$ is cyanomethyl.

21. An insecticidal, acaricidal or nematicidal composition comprising an insecticidally, acaricidially or nematicadally effective amount of a compound according to claim 1 and a carrier or diluent therefor.

22. A method of containing and controlling insect, acarine or nematode pests at a locus which comprises treating the pests or the locus of the pests with an effective amount of a composition according to claim 21.

23. A method according to claim 22 wherein the pests are insects pests of growing plants.

* * * * *